(12) United States Patent
Yamada et al.

(10) Patent No.: US 6,838,465 B2
(45) Date of Patent: Jan. 4, 2005

(54) N-ACYLTETRAHYDROISOQUINOLINE DERIVATIVES

(75) Inventors: Koji Yamada, Tsukuba (JP); Masaaki Hirose, Tsukuba (JP); Hisashi Iwaasa, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 69 days.

(21) Appl. No.: 10/275,712

(22) PCT Filed: Apr. 27, 2001

(86) PCT No.: PCT/JP01/03736
§ 371 (c)(1),
(2), (4) Date: Jan. 9, 2003

(87) PCT Pub. No.: WO01/85693
PCT Pub. Date: Nov. 15, 2001

(65) Prior Publication Data
US 2004/0044031 A1 Mar. 4, 2004

(30) Foreign Application Priority Data
May 11, 2000 (JP) ........................................ 2000-137923

(51) Int. Cl.⁷ .................. A61K 31/4725; A61K 31/506; C07D 217/06; C07D 401/12
(52) U.S. Cl. ....................... 514/307; 544/238; 546/146; 514/252.04; 514/307
(58) Field of Search .................. 546/146; 544/238; 514/307, 252.04

(56) References Cited

FOREIGN PATENT DOCUMENTS

| EP | 0675112 | * 4/1995 | ......... C07D/233/54 |
|---|---|---|---|
| EP | 0 675 112 A1 | 10/1995 | |
| WO | WO 92/12132 | 7/1992 | |
| WO | WO 96/39384 | 12/1996 | |
| WO | WO-9639384 | * 12/1996 | ......... C07D/209/42 |
| WO | WO 99/09024 | 2/1999 | |
| WO | 99/23078 A2 | 5/1999 | |
| WO | WO 99/58533 | 11/1999 | |

OTHER PUBLICATIONS

Accession No. 2001:904039 CHEMCATS listing of ComGenex Product List, RN 336858–32–3, published in 2001.*
Answer 1 of 15 Registry Copyright 2002 ACS, RN 292028–76–3 Registry, "Ring System Data".

* cited by examiner

*Primary Examiner*—Ceila Chang
*Assistant Examiner*—Janet L Coppins
(74) *Attorney, Agent, or Firm*—Nixon & Vanderhye P.C.

(57) ABSTRACT

This invention relates to novel compounds represented by the general formula [I]:

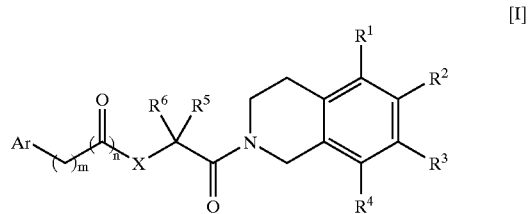

(wherein, $R^1$ and $R^4$ are the same or different, and represent hydrogen atoms, lower alkyl groups or the like; $R^2$ and $R^3$ are the same or different, and represent lower alkoxy groups or lower alkyl groups; $R^5$ represents a lower alkyl group or aralkyl group optionally having substituent(s); $R^6$ represents a hydrogen atom or a lower alkyl group; X represents O, S or NH; m represents an integer of 0 to 3; n represents an integer of 0 or 1; and Ar represents a phenyl group or heteroaryl group optionally having substituent(s)).

The compounds of the invention have an antagonistic action on orexin receptors, and are useful for treatment of appetite abnormality, obesity, sleeping disorder or the like.

6 Claims, No Drawings

N-ACYLTETRAHYDROISOQUINOLINE DERIVATIVES

TECHNICAL FIELD

This invention relates to novel tetrahydroisoquinoline derivatives or pharmaceutically acceptable salts thereof useful as orexin receptor antagonists in the pharmaceutical field, and their use.

BACKGROUND ART

Two novel neuropeptides in the brain, orexin-A and orexin-B were found lately as intrinsic ligands (Japanese Laid-open Patent Publication No. 10-229887; Cell, Vol. 92, 573–585, 1998) of G-protein coupled receptors, that is, orexin receptors mainly existing in the brain (WO 96/34877, Japanese Laid-open Patent Publication Nos. 10-327888, 10-327889 and 11-178588, etc.), and their biological functions draw attention.

It is also known that there are two subtypes in orexin receptors, namely, $OX_1$ receptor (OX1R) as type-1 subtype and $OX_2$ receptor (OX2R) as type-2 subtype.

At first, it is presumed for the reasons of the following (1) to (3) that orexins have something to do with control of feeding behavior. Namely, (1) the mRNA of prepro-orexin as the common precursor of orexin A and orexin B, and orexin immune reaction localize in the lateral hypothalamic region known as the feeding center from long ago (Handbook of the Hypothalamus, Vol. 2; Phisiology of the Hypothalamus, 557–620, 1980), (2) in rats fasted for 48 hours, the amount of prepro-orexin mRNA in the hypothalamus increases about 2.5 times compared with that under no fast, and (3) when a catheter is made to indwell in the lateral ventricle of a rat and orexin A or orexin B is administered, the amount of the food intake increases.

From experiments made using various animals, it is presumed that orexins participate not only in feeding behavior but also in various physiological actions such as emotional behavior, metabolism control, blood pressure control, hormone secretion control, body temperature control, sleep and awakening, secretion of stomach acids, control of the pain sensation (Idenshi Igaku, Vol.2, No.4, 618–620, 1998; Journal of Neuroscience, Vol.18, No.19, 7362–7971, 1998; Journal of Neuroscience, Vol.18, No.23, 9996–10015, 1998; Journal of Neuroscience, Vol.18, No.23, 9996–10015, 1998; Journal of Neuroscience, Vol.19, No.3, 1072–1087, 1999; Biochemical and Biophysical Research Communications, Vol.254, No.3, 623–627, 1999; Journal of Neuroscience, Vol.19,No.8, 3171–3182, 1999).

Lately, it was reported, based on experiments using dogs genetically falling in narcolepsy (Cell, Vol.98, 365–376, 1999) and experiments using mice lacking orexin (Cell, Vol.98, 437–451, 1999), that $OX_2$ receptor, one of the two subtypes of orexin receptors, participates in narcolepsy.

Further, there is a report that in 7 patients among 9 patients of human narcolepsy, orexins in the cerebrospinal fluid, detectable in healthy individual, are lowered up to less than the detection limit (Lancet, Vol.355, 39–40, 2000), which suggests that also in humans, orexins have something to do with narcolepsy.

These various physiological actions in which orexins are presumed to participate are thought to be expressed via one or both of $OX_1$ receptor and $OX_2$ receptor as the two subtypes of orexin receptors.

As to compounds showing an antagonistic action on one or both of the two subtypes ($OX_1$ receptor and $OX_2$ receptor) of orexin receptors, one report has so far been made (WO 99/09024), but compounds disclosed in WO 99/09024 have phenylurea structure utterly different from tetrahydroisoquinoline structure which the compounds of the present invention have, and, moreover, in the WO, only antagonistic action on the $OX_1$ receptor (HFGAN72 receptor) is shown, and antagonistic action on the $OX_2$ receptor is not shown at all.

As compounds analogous in structure to the compounds of the invention, compounds represented by the following structural formula [II]:

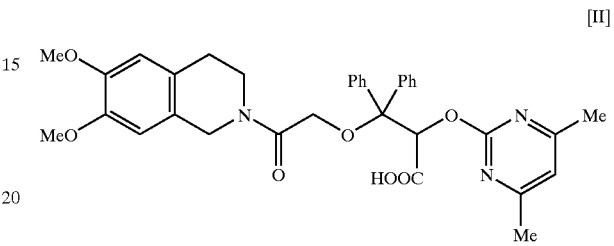

are disclosed in WO 99/23078 (hereinafter abbreviated as Document A). The compounds represented by the structural formula [II] in Document A have a tetrahydroisoquinoline ring bearing methoxy groups at the 6- and 7-positions as in the compounds of the invention, but do not have a branch at the α-position of the carbonyl group at the 2-position, and, in addition, are clearly different from the compounds of the invention in the side chain structure. Moreover, the compounds disclosed in Document A are described as endothelin antagonists, and in action, Document A has nothing to do with the present invention. Further, compounds represented by the following structural formula [III]:

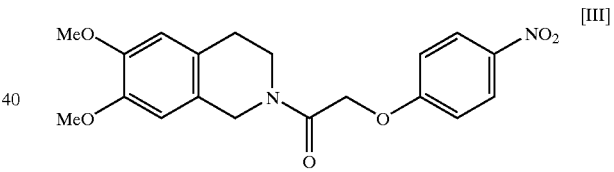

are disclosed in Japanese Laid-open Patent Publication (Tokuhyo-hei) No. 6–506440 (hereinafter abbreviated as Document B) as intermediates of the invention compounds described in Document B. The compounds represented by the structural formula [III] in Document B have a tetrahydroisoquinoline ring bearing methoxy groups at the 6- and 7-positions, but do not have a branch at the α-position of the carbonyl group at the 2-position, as in the compounds described in Document A, and are clearly different from the compounds of the present invention.

DISCLOSURE OF INVENTION

For elucidation of functions of orexins and orexin receptors presumed to participate in various physiological actions such as, for example, ingestion behavior, control of emotional behavior, metabolism control, blood pressure control, hormone secretion control, body temperature control, sleep and awakening, secretion of stomach acids, and control of the sense of pain, compounds showing an antagonistic action on one or both of the two subtypes ($OX_1$ receptor and $OX_2$ receptor) of orexin receptors are important. This invention aims to provide compounds which show a selective antagonistic action on a subtype ($OX_2$ receptor) and are effective for elucidation of physiological actions of orexin receptors and improvement of pathologic states with which orexin receptors are involved.

The present inventors intensely studied for solving the above problems, and as a result, they found that novel tetrahydroisoquinoline derivatives represented by the following general formula [I] and their salts have a selective antagonistic action on the $OX_2$ receptor, one of orexin receptor subtypes, and completed the invention.

Namely, the invention relates to a compound represented by the general formula (I):

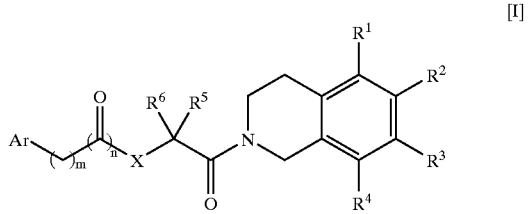

(wherein, $R^1$ and $R^4$, each independently, represent hydrogen atoms, lower alkoxy groups or lower alkyl groups; $R^2$ and $R^3$, each independently, represent lower alkoxy groups or lower alkyl groups; $R^5$ represents an aralkyl group optionally having substituent(s) selected from the group consisting of lower alkyl group(s), lower alkoxy group(s), halogen atom(s), halogenated lower alkyl group(s), hydroxyl group(s), carboxyl group(s), lower alkoxycarbonyl group(s), nitro group(s), amino group(s), lower alkylamino group(s), cyano group(s) and methylenedioxy group(s), or represents a lower alkyl group optionally having substituent(s) selected from the group consisting of lower alkoxy group(s), hydroxyl group(s) and halogen atom(s); $R^6$ represents a hydrogen atom or a lower alkyl group; X represents O, S or NH; m represents an integer of 0 to 3; n represents an integer of 0 or 1; Ar represents a monocyclic or bicyclic aryl or heteroaryl group optionally having substituent(s) selected from the group consisting of lower alkyl group(s), lower alkoxy group(s), halogen atom(s), halogenated lower alkyl group(s), hydroxyl group(s), carboxyl group(s), lower alkoxy carbonyl group(s), nitro group(s), amino group(s), lower alkylamino group(s), cyano group(s) and methylenedioxy group(s)), or a pharmaceutically acceptable salt thereof, and its use.

Detailed description is made below on the general formula [I].

First, description is made on terms in the present specification.

In the specification, "lower alkyl group" represents a straight-chain or branched alkyl group having 1 to 6 carbon atoms, and includes, for example, a methyl group, an ethyl group, a propyl group, an isopropyl group, a butyl group, an isobutyl group, a sec-butyl group, a tert-butyl group, a pentyl group, an isoamyl group, a neopentyl group, a 1,1-dimethylpropyl group, a 1-methylbutyl group, a 2-methylbutyl group, a 1,2-dimethylpropyl group, a hexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, 1,2,2-trimethylpropyl group, 1-ethyl-2-methylpropyl group, etc.

"Lower alkoxy group" represents a straight-chain or branched alkoxy group having 1 to 6 carbon atoms, and includes, for example, a methoxy group, an ethoxy group, a propoxy group, an isopropoxy group, a butoxy group, an isobutoxy group, a sec-butoxy group, a tert-butoxy group, a pentyloxy group, an isoamyloxy group, a 1,1-dimethylpropoxy group, a neopentyloxy group, a 2-methylbutoxy group, a 1,2-dimethylpropoxy group, a 1-ethylpropoxy group, a hexyloxy group, etc.

"Halogen atom" represents a fluorine atom, a chlorine atom, a bromine atom or an iodine atom.

"Halogenated lower alkyl group" represents a straight-chain or branched halogenated alkyl group having 1 to 6 carbon atoms, and includes, for example, a fluoromethyl group, a bromomethyl group, a difluoromethyl group, a dichloromethyl group, a trifluoromethyl group, a trichloromethyl group, a chlorodifluoromethyl group, a 2,2,2-trifluoroethyl group, a pentafluoroethyl group, etc.

"Loweralkoxycarbonyl group " represents a straight-chain or branched alkoxycarbonyl group having 1 to 6 carbon atoms, and includes, for example, a methoxycarbonyl group, an ethoxycarbonyl group, an n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentoxycarbonyl group, an isopentoxycarbonyl group, etc.

"Lower alkylamino group" represents a straight-chain or branched alkylamino group having 1 to 6 carbon atoms, and includes, for example, a methylamino group, an ethylamino group, a dimethylamino group, an diethylamino group, a propylamino group, a tert-butylamino group, a pentylamino group, a 1,1-dimethylbutylamino group, etc.

"Aralkyl group" includes, for example, a benzyl group, a 1-phenylethyl group, a 3-phenylpropyl group, a 2-phenylpropyl group, a 1-phenylpropyl group, a 1-methyl-2-phenylethyl group, a 4-phenylbutyl group, a 3-phenylbutyl group, a 2-phenylbutyl group, a 1-phenylbutyl group, a 2-methyl-3-phenylpropyl group, a 2-methyl-2-phenylpropyl group, a 2-methyl-1-phenylpropyl group, a 1-methyl-3-phenylpropyl group, a 1-methyl-2-phenylpropyl group, a 1-methyl-1-phenylpropyl group, a 1-ethyl-2-phenylethyl group, a 1,1-dimethyl-2-phenylethyl group, a 5-phenylpentyl group, a 4-phenylpentyl group, a 3-phenylpentyl group, a 2-phenylpentyl group, a 1-phenylpentyl group, a 3-methyl-4-phenylbutyl group, a 3-methyl-3-phenylbutyl group, a 3-methyl-2-phenylbutyl group, a 3-methyl-1-phenylbutyl group, a 6-phenylhexyl group, a 5-phenylhexyl group, a 4-phenylhexyl group, a 3-phenylhexyl group, a 2-phenylhexyl group, a 1-phenylhexyl group, a 4-methyl-5-phenylpentyl group, a 4-methyl-4-phenylpentyl group, a 4-methyl-3-phenylpentyl group, a 4-methyl-2-phenylpentyl group, a 4-methyl-1-phenylpentyl group, etc.

Further detailed description is made on the general formula [I].

$R^1$ and $R^4$, each independently, represent hydrogen atoms, lower alkoxy groups or lower alkyl groups. Among them, $R^1$ and $R^4$ are preferably hydrogen atoms. $R^2$ and $R^3$, each independently, represent lower alkoxy groups or lower alkyl groups. Among them, $R^2$ and $R^3$ are preferably lower alkoxy groups, more preferably a methoxy group.

$R^5$ represents an aralkyl group or lower alkyl group optionally having substituent(s).

"An aralkyl group optionally having substituent(s) selected from the group consisting of lower alkyl group(s), lower alkoxy group(s), halogen atom(s), halogenated lower alkyl group(s), hydroxyl group(s), carboxyl group(s), lower alkoxycarbonyl group(s), nitro group(s), amino group(s), lower alkylamino group(s), cyano group(s) and methylenedioxy group(s)" represented by $R^5$ means the above-mentioned aralkyl group having no substituent or the above-mentioned aralkyl group having substituent(s) at substitutable position(s). The substituent(s) can be the same or different, one or two or more, preferably one or two selected from the group consisting of lower alkyl groups, lower alkoxy groups, halogen atoms, halogenated lower alkyl groups, a hydroxyl group, a carboxyl group, lower alkoxycarbonyl groups, a nitro group, an amino group, lower alkylamino groups, a cyano group and a methylenedioxy group.

"A lower alkyl group optionally having substituent(s) selected from the group consisting of lower alkoxy group(s), hydroxyl group(s) and halogen atom(s)" represented by $R^5$ means the above-mentioned alkyl group having no substituent or the above-mentioned alkyl group having substituent(s) at substitutable position(s). The substituent(s) can be the same or different, one or two or more, preferably one or two selected from the group consisting of lower alkoxy groups, a hydroxyl group and halogen atoms.

Among them, $R^5$ is preferably an aralkyl group having no substituent or an alkyl group having no substituent, more preferably a benzyl group or a tert-butyl group.

$R^6$ represents a hydrogen atom or a lower alkyl group, and preferred among them is a hydrogen atom.

X represents O, S or NH, and preferred among them is NH.

m represents an integer of 0 to 3, and n represents an integer of 0 or 1.

Among them, it is preferred that m and n are 0 or 1, and it is more preferred that m is 0 and n is 1, or m is 1 and n is 0.

"A monocyclic or bicyclic aryl or heteroaryl group" represented by Ar represents an aryl group such as a phenyl group or a naphthyl group, or represents an aromatic monocyclic heterocyclic group such as a furyl group, a thienyl group, a pyrrolyl group, an oxazolyl group, an isoxazolyl group, a thiazolyl group, an isothiazolyl group, an imidazolyl group, a pyrazolyl group, a pyridinyl group, a pyridazinyl group, a pyrimidinyl group or a pyrazinyl, or represents an aromatic condensed heterocyclic group such as a benzofuranyl group, an isobenzofuranyl group, a benzo[b]thienyl group, an indolyl group, an isoindolyl group, a 1H-indazolyl group, a benzimidazolyl group, a benzoxazolyl group, a 1,2-benzisoxazolyl group, a benzothiazolyl group, a 1,2-benzisothiazolyl group, a quinolyl group, an isoquinolyl group, a quinazolinyl group or a quinoxalinyl group. Preferred among them is a phenyl group, a naphthyl group, a furyl group, a thienyl group, a thiazolyl group, an isothiazolyl group, an oxazolyl group, an isoxazolyl group, a pyridinyl group, a pyrazolyl group, a pyrrolyl group, a pyrimidinyl group, a quinolyl group, a quinoxalinyl group, an isoquinolyl group, a pyrazinyl group, an indolyl group, a benzothiazolyl group or a benzimidazolyl group; further preferred among them is a phenyl group, a furyl group, a thienyl group, a thiazolyl group, an isothiazolyl group, an oxazolyl group, an isoxazolyl group, a pyridinyl group, a pyrazolyl group, a pyrrolyl group, a quinolyl group, a quinazolinyl group, an isoquinolyl group or a pyrazinyl group; and particularly preferred among them is a phenyl group, a furyl group, a thienyl group, a thiazolyl group, a pyridinyl group, a quinolyl group or a pyrrolyl group.

"A monocyclic or bicyclic aryl or heteroaryl group optionally having substituent(s) selected from the group consisting of lower alkyl group(s), lower alkoxy group(s), halogen atom(s), halogenated lower alkyl group(s), hydroxyl group(s), carboxyl group(s), lower alkoxy carbonyl group(s), nitro group(s), amino group(s), lower alkylamino group(s), cyano group(s) and methylenedioxy group(s)" represented by Ar means the above-mentioned aryl or heteroaryl group having no substituent, or the above-mentioned aryl or heteroaryl group having substituent(s) at substitutable position(s). The substituent(s) can be the same or different, one or two or more, preferably one or two selected from the group consisting of lower alkyl groups, lower alkoxy groups, halogen atoms, halogenated lower alkyl groups, a hydroxyl group, a carboxyl group, lower alkoxycarbonyl groups, a nitro group, an amino group, lower alkylamino groups, a cyano group and a methylenedioxy group.

The compounds of the invention can be present in the forms of pharmaceutically acceptable salts, and such salts can be prepared according to conventional processes, using the compounds of the general formula [I]. As such salts, there can be mentioned acid addition salts, for example, hydrohalogenic acid salts such as hydrochlorides, hydrofluorides, hydrobromides and hydroiodides; inorganic acid salts such as nitrates, perchlorates, sulfates, phosphates and carbonates; lower alkyl sulfonates such as methanesulfonates, trifluoromethanesulfonates and ethanesulfonates; aryl sulfonates such as benzenesulfonates and p-toluenesulfonates; organic acid salts such as fumarates, succinates, citrates, tartrates, oxalates and maleates; amino acid salts such as glutamates and aspartates. The compounds of the invention can exist as any hydrates or solvates of free compounds or their salts.

The compounds of the invention represented by the general formula [I] can sometimes exist as optical isomers due to asymmetric carbon atom(s), depending on the substituent(s) of $R^5$ and $R^6$. It goes without saying that all these optical isomers are included in the compounds of the invention. It also goes without saying that any mixtures of these optical isomers or any mixtures of these racemates are included in the invention.

A compound [I-a] of the invention can be synthesized, for example, according to the following process.

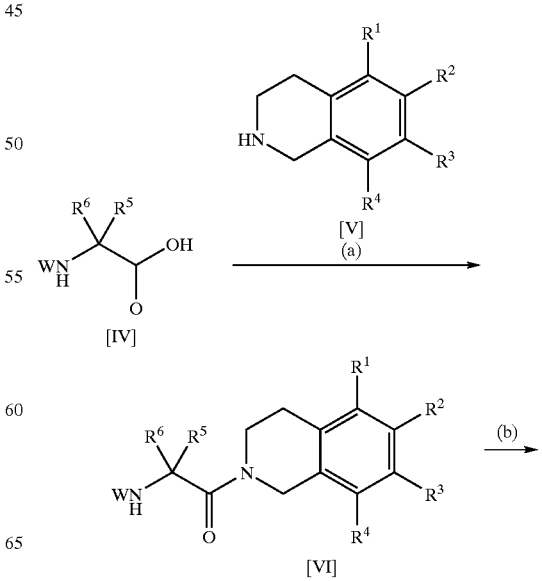

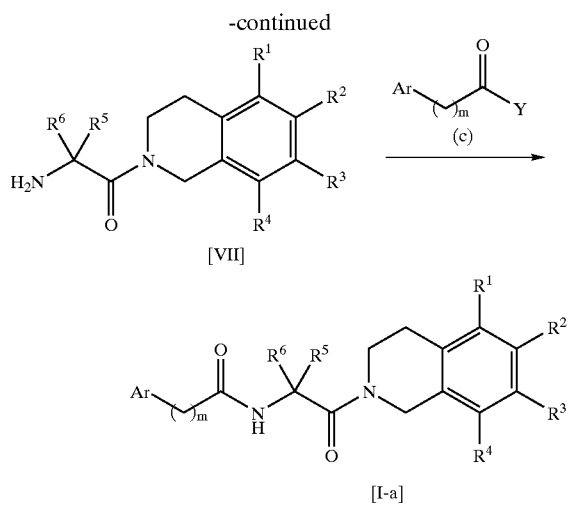

(wherein, $R^1$ to $R^6$, Ar and m are as defined above, W represents a protective group for an amino group, and Y represents a halogen atom or a hydroxyl group)

An α-amino acid derivative [IV] having a protective group W on the amino group can be synthesized from a known α-amino acid or an α-amino acid obtainable based on a known process. As the protective group W of the amino group of the compound represented by [IV], any one can be used, without being particularly limited, so long as it acts as a protective group in the step (a) of the above formulae and can readily be removed according to the step (b). Such protective groups can appropriately be selected by one skilled in the art, for example according to the method described in T. W. Green and P. G. M. Wuts, "Protective Groups in Organic Synthesis", 1991, and include, for example Boc group (tert-butoxycarbonyl group), Fmoc group (fluorenylmethyloxycarbonyl group), Bn group (benzyl group), Z group (benzyloxycarbonyl group), Alloc group (allyloxycarbonyl group), etc. Introduction of Boc group can, for example, be carried out by making $Boc_2O$ acting in the presence of a base such as triethylamine, and introduction of Z group can, for example, be carried out by making benzyl chloroformate acting in the presence of a base such as sodium hydroxide. The step (a) is a dehydration condensation reaction between a compound [IV] having a carboxyl group and a tetrahydroisoquinoline compound [V]. In the reaction, the compound [V] is used preferably in an amount of 0.8 to 1.2 equivalents per 1 equivalent of the compound [IV]. The dehydration condensation reaction can be carried out by a conventional amide formation reaction, for example according to the processes described in "Pepuchido Gosei no Kiso to Jikken" (Foundations and Experiments of Peptide Syntheses) (Nobuo IZUMIYA et al., Maruzen, 1983), etc. Namely, the reaction can be carried out using a well-known condensing agent, or by an active ester method, a mixed acid anhydride method, an acid chloride method, a carbodiimide method or the like utilizable by one skilled in the art. More specifically, as such amide forming reagents, there can, for example, be used dicyclohexylcarbodiimide, 1-ethoxycarbonyl-2-ethoxy-1,2-dihydroquinoline, 1-cyclohexyl-3-(2-morpholinylethyl)carbodiimide, N,N-carbonyldiimidazole, diphenylphosphoric acid azide, 2-chloro-1,3-dimethyl-2-imidazolium chloride, bromotripyrrolidinophosphonium hexafluorophosphate (PyBrop), diethyl cyanophosphate, 1-ethyl-3-(3-dimethylaminopropyl)carbodiimide hydrochloride, etc. The amide forming reagent is usually used in an amount of 1 to 5 equivalents, preferably 1 to 2 equivalents per 1 equivalent of the compound [IV].

The amide bond forming reaction can also be carried out by condensing the compound [IV] with addition of a phenol such as, for example, 2,4,5-trichlorophenol, pentachlorophenol, pentafluorophenol, 2-nitrophenol or 4-nitrophenol, or an N-hydroxy derivative such as, for example, N-hydrosuccinimide, 1-hydroxybenzotriazole, N-hydroxypiperidine or N-hydroxy-5-norbomene-2,3-dicarbodiimide, and further with addition of dicyclohexylcarbodiimide, 1-ethyl-3-(3-dimethylaminopropyl)carbodiimide hydrochloride or the like, to convert the compound [IV] to an active ester, and then reacting the active ester with the compound [V]. The phenol or N-hydroxy derivative is used usually in an amount of 1 to 3 equivalents per 1 equivalent of the compound [IV]. Dicyclohexylcarbodiimide or 1-ethyl-3-(3-dimethylaminopropyl)carbodiimide hydrochloride or the like is used usually in an amount of 1 to 3 equivalents per 1 equivalent of the compound [IV]. The condensation reaction can, if necessary, be accelerated by adding an organic base, for example a tertiary amine such as triethylamine, pyridine or N-methylpiperidine. Such a reaction accelerator is used usually in an amount of 1 to 3 equivalents per 1 equivalent of the compound [IV]. In addition to the above organic base, in the condensation reaction, it is usually possible to use a catalytic amount of 4-(N,N-dimethylamino)pyridine, 4-pyrrolidinopyrrolidine or the like. For making the reaction proceed efficiently, it is also possible to use a quaternally ammonium salt such as tetrabutylammonium chloride or benzyltriethylammonium chloride, or the like usually in an amount of 0.1 to 1 equivalent per 1 equivalent of the compound [IV]. There is no particular limitation about the reaction temperature and reaction time, but the reaction is carried out at a reaction temperature of the order of −20 to 50° C., preferably 0 to 20° C. for a time of the order of 1 to 15 hours, preferably 1 to 5 hours. The thus obtained tetrahydroisoquinoline derivative [VI] can be isolated and purified, according to conventional methods, by known separation and purification means such as, for example, concentration, concentration under reduced pressure, crystallization, solvent extraction, reprecipitation, chromatography, etc. After the condensation, the protective group W is removed according to the step (b), and the reaction conditions of this step can appropriately be selected by one skilled in the art, depending on the kinds and properties of the protective groups used. As methods of removal of the protective groups, methods known per se or methods based on them can be used. For example, when Z group or the like is used as the protective group, it can readily be removed by hydrogenolyzing the compound [VI] using an appropriate catalytic hydrogenation catalyst, and when Boc group is used as the protective group, it can readily be removed by treating the compound [VI] with an acid such as hydrochloric acid or trifluoroacetic acid.

The step (c) is a step of condensing the amine compound, and a compound [I-a] of the invention can be obtained by the same condensation method as described in the above step (a). The thus obtained compound [I-a] of the invention can be isolated and purified, according to conventional methods, by known separation and purification means such as, for example, concentration, concentration under reduced pressure, crystallization, solvent extraction, reprecipitation, chromatography, etc. The reaction solvents used in the condensation reactions of the above step (a) and step (c) are not particularly limited so long as it does not badly influence the reaction, but inert solvents are preferred. As such solvents, there can, for example, be mentioned halogenated hydrocarbons such as dichloromethane and chloroform, ethers such as ether and tetrahydrofuran, amides such as dimethylformamide and dimethylacetamide, nitriles such as acetonitrile and propiononitrile, and mixed solvents thereof.

A compound [I-a] of the invention can also be prepared, for example by the following process.

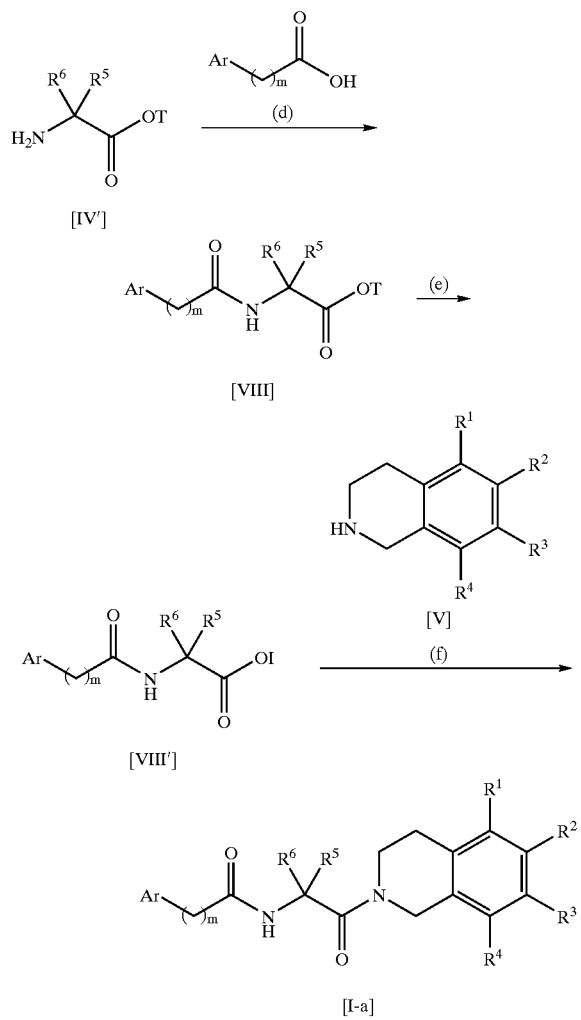

(wherein, T represents a protective group for a carboxyl group, and the other symbols have the same meanings as defined above)

The amino acid derivative [IV'] used in the step (d) can be synthesized according to a known method or a method based on it. As the protective group T for the carboxyl group shown in [IV'], any protective group can be used, without being particularly limited, so long as it acts as a protective group in the step (d) of the above formulae and can readily be removed according to the step (e). Such protective groups can appropriately be selected by one skilled in the art, for example according to the method described in the aforementioned Protective Groups in Organic Synthesis, 1991, and include, for example alkyl groups such as a methyl group, an ethyl group and a tert-butyl group, alkenyl groups such as an allyl group, aralkyl groups such as a benzyl group and a p-methoxybenzyl group, etc. The step (d) is an amide bond formation reaction, and can be carried out using the same method as in the above step (a) or a method based on it. After the amide bond formation reaction, the protective group T is removed according to the step (e). The step (f) is an amide bond formation reaction, and can be carried out by the same method as in the above step (a) or a method based on it. The thus obtained tetrahydroisoquinoline derivative [I-a] can be isolated and purified, according to conventional methods, by known separation and purification means such as, for example, concentration, concentration under reduced pressure, crystallization, solvent extraction, reprecipitation, chromatography, etc.

A compound [I-b] of the invention can, for example, be synthesized by the following process or the like.

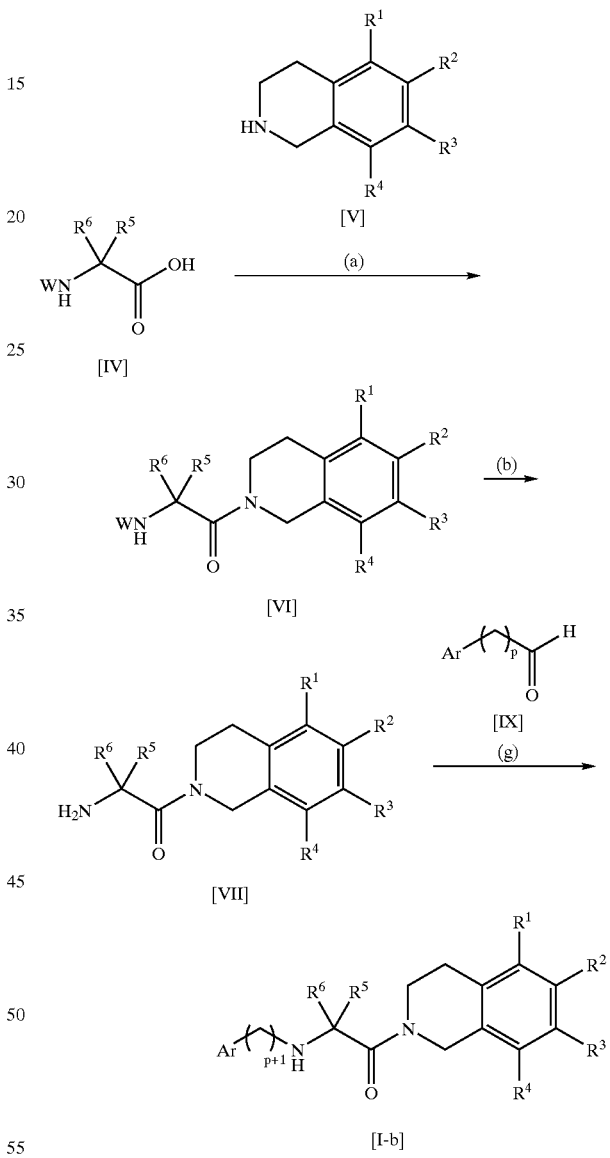

(wherein, p represents an integer of 0 to 2, and the other symbols have the same meanings as defined above)

In the step (g), a compound [VII] obtained in the above steps (a) and (b) is subjected to reductive alkylation using an aldehyde compound [IX] to prepare a compound [I-b], a compound of the invention. This reductive alkylation reaction can be carried out according to a known method, and is carried out by reacting the compound [VII] having an amino group with the aldehyde compound [IX], and treating the resulting imine, as such or after isolation, with a reducing agent. In the reaction, the aldehyde compound [IX] is used in an amount of usually 0.5 to 3 equivalents, preferably 0.8 to 1.2 equivalents per 1 equivalent of the compound [VII]. As the reducing agent used, there can, for example, be mentioned alkali metal borohydrides such as sodium borohydride, lithium borohydride and sodium triacetoxyborohydride. The reducing agent is used in an amount of usually 1 to 10 equivalents, preferably 1 to 4 equivalents per 1 equivalent of the compound [VII]. As a solvent used in the reaction, an organic solvent not badly influencing the reaction is used, and such organic solvent includes halogenated hydrocarbons such as dichloromethane and chloroform, ethers such as diethyl ether, tert-butyl methyl ether and tetrahydrofuran, amides such as dimethylformamide and dimethylacetamide, nitriles such as acetonitrile and propiononitrile, alcohols such as methanol, ethanol and propanol, aromatic hydrocarbons such as benzene, toluene and xylene and mixed solvents thereof. There is no particular limitation about the reaction temperature and reaction time, but the reaction is carried out at a reaction temperature of −60 to 50° C., preferably −20 to 20° C. for 1 to 40 hours, preferably 1 to 10 hours. The thus obtained tetrahydroisoquinoline derivative [I-b] as a compound of the invention can be isolated and purified, according to conventional methods, by known separation and purification means such as, for example, concentration, concentration under reduced pressure, crystallization, solvent extraction, reprecipitation, chromatography, etc.

A compound [I-b] of the invention can also be prepared, for example by the following process.

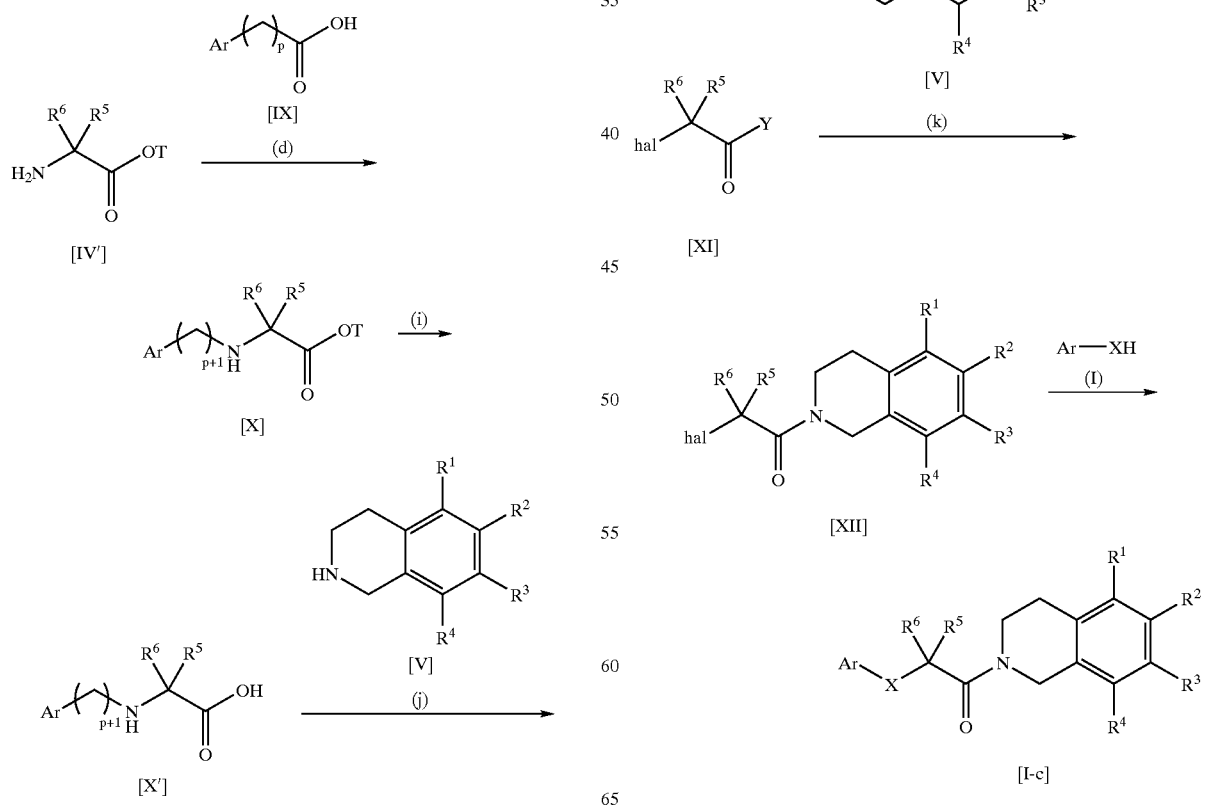

(wherein, p represents an integer of 0 to 2, and the other symbols have the same meanings as defined above)

In the step (h), the compound [IV'] is condensed with an aldehyde compound [IX] by reductive alkylation reaction, then in the step (i), the protective group of the carboxyl group is removed, and further in the step (j), an amide bond formation reaction is carried out to prepare a compound [X]. These steps can be carried out according to the above-mentioned method or a method based on it. The thus obtained tetrahydroisoquinoline derivative [I-b] as a compound of the invention can be isolated and purified, according to conventional methods, by known separation and purification means such as, for example, concentration, concentration under reduced pressure, crystallization, solvent extraction, reprecipitation, chromatography, etc.

A compound [I-c] of the invention can be prepared by the following process.

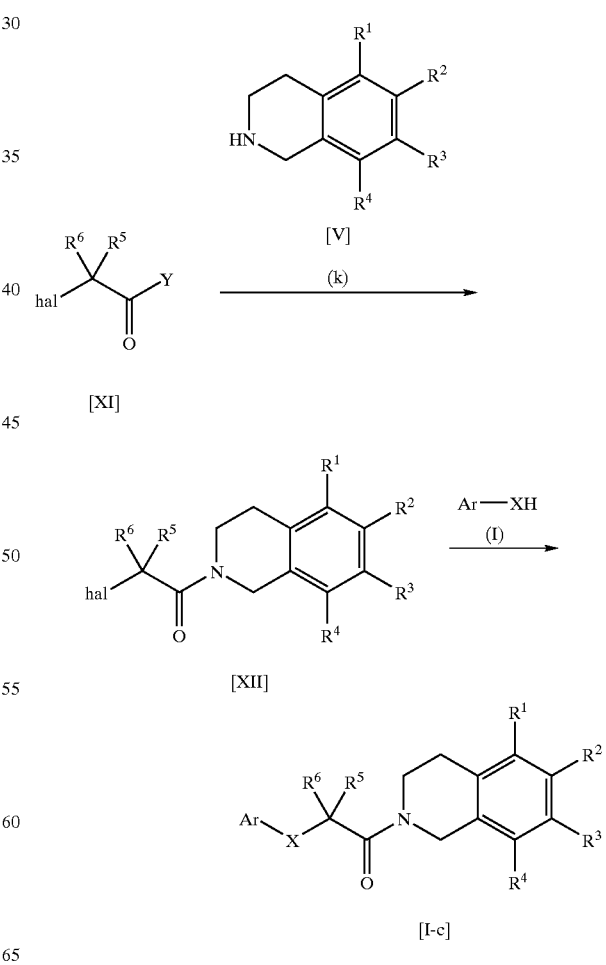

(wherein, hal represents a halogen atom, Y represents a halogen atom or a hydroxyl group, and the other symbols have the same meanings as defined above)

In the step (k), a tetrahydroisoquinoline derivative [V] is condensed with an α-halocarboxylic acid derivative [XI] to prepare an amide derivative [XII]. This step can be carried out using the same process as in the aforementioned amide bond formation reaction or a process based on it, and a solvent to be used is not particularly limited so long as it does not badly influence the reaction, and solvents used in the aforementioned amide bond formation reaction can be used.

In the step (1), the obtained amide derivative [XII] is reacted with a compound Ar—XH, if necessary using a base, to prepare a compound [I-c], of the invention. As the base, sodium hydride, potassium hydride, sodium amide or the like is used, and the use amount of such a base is usually 1 to 10 equivalents, preferably 1 to 3 equivalents per 1 equivalent of the compound [XII]. A solvent to be used in the step (1) is not particularly limited so long as it does not badly influence the reaction, but is preferably an inert solvent, and the solvent used in the above step (k) can be used. There is no particular limitation about the reaction temperature and reaction time, but it is preferred that the reaction is carried out at a reaction temperature of around room temperature for 1 to 40 hours, preferably 1 to 10 hours. The thus obtained tetrahydroisoquinoline derivative [I-c] can be isolated and purified, according to conventional methods, by known separation and purification means such as, for example, concentration, concentration under reduced pressure, crystallization, solvent extraction, reprecipitation, chromatography, etc.

A compound [I-c] of the invention can also be prepared by the following process.

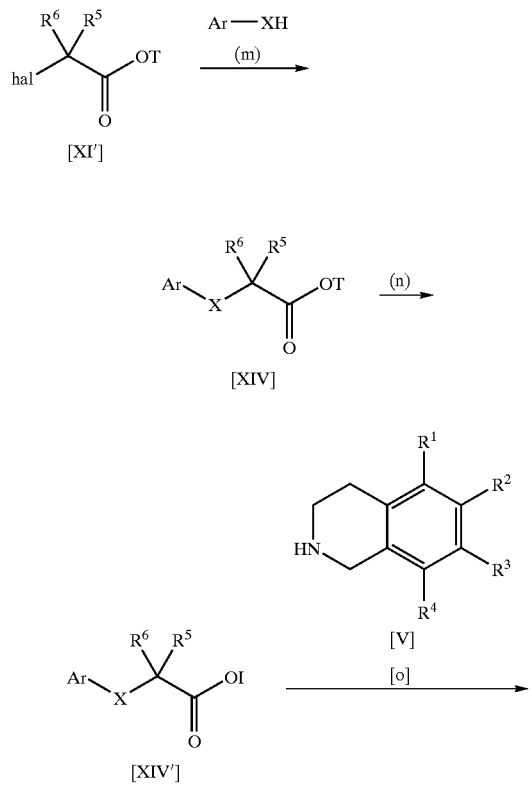

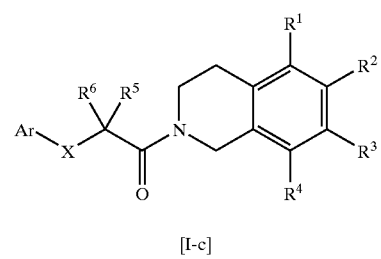

[I-c]

(wherein, each symbol has the same meaning as defined above)

In the step (m), an α-halocarboxylic acid derivative[XI'] is reacted with a compound Ar—XH, then in the step (n), the protective group of the carboxyl group is removed, and further in the step (o), an amide bond formation reaction is carried out to synthesize a compound [I-c] of the invention. Each of these steps can be carried out by the aforementioned process or a process based on it. The thus obtained tetrahydroisoquinoline derivative [I-c], a compound of the invention, can be isolated and purified, according to conventional methods, by known separation and purification means such as, for example, concentration, concentration under reduced pressure, crystallization, solvent extraction, reprecipitation, chromatography, etc.

Further, compounds [I-d], [I-e] and [I-f], etc., compounds of the invention, included in the above [I-c] can also be prepared by the following process.

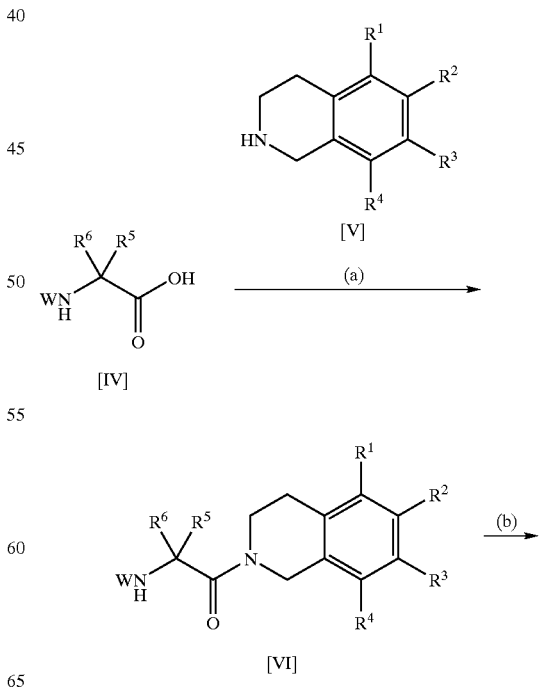

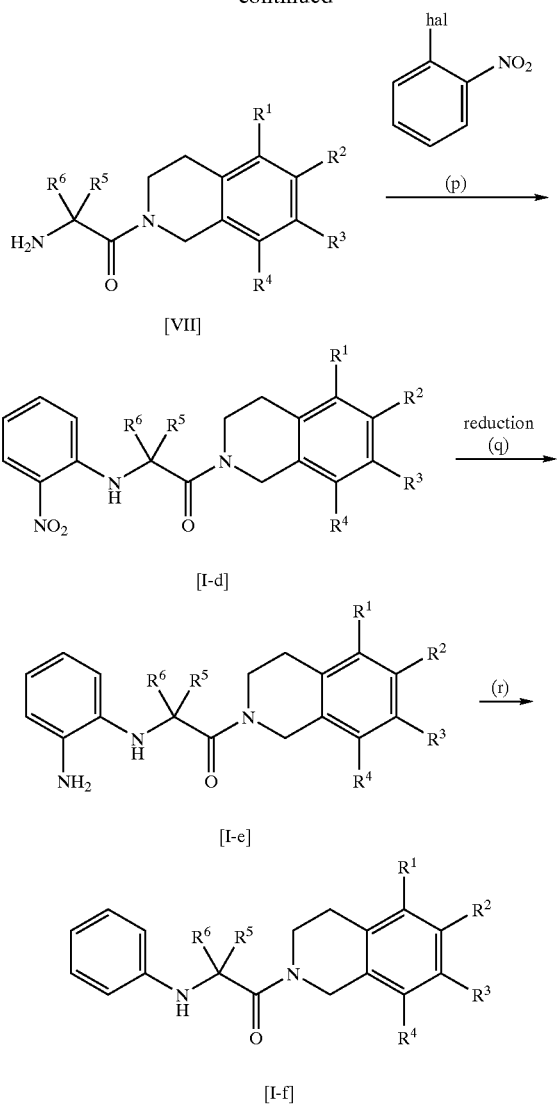

(wherein, each symbol has the same meaning as defined above)

In the step (p), the amine derivative [VII] obtained by the above steps (a) and (b) is reacted with an o-halonitrobenzene in the presence of a base to carry out condensation reaction. It is preferred that hal is a fluorine atom. As the base to be used, there can, for example, be mentioned sodium hydroxide, potassium hydroxide, alkali metal salts such as potassium carbonate, sodium carbonate and sodium bicarbonate, amines such as pyridine, triethylamine and N,N-dimethylaniline, metal hydrides such as sodium hydride and potassium hydride, etc. Such a base is used in an amount of usually 1 to 10 equivalents, preferably 1 to 3 equivalents per 1 equivalent of the compound [VII]. A reaction solvent used in the step (p) is not particularly limited so long as it does not badly influence the reaction, but an inert solvent is preferred, and as the solvent, a solvent used in the step (c), etc. can be used. There is no particular limitation about the reaction temperature and reaction time, but the reaction is carried out at a reaction temperature of the order of room temperature to 200° C., preferably 20 to 100° C. for a time of the order of 1 to 20 hours, preferably 1 to 5 hours. In the step (q), the nitrobenzene derivative [I-d] is reduced to give the aniline derivative [I-e]. The reduction reaction of the step (q) is carried out according to a reaction well known by one skilled in the art, for example by a method using a metal such as iron or tin, a method using a phosphine such as triphenylphosphine, or by catalytic hydrogenation reduction. The reducing agent is used in an amount of usually 1 to 50 equivalents, preferably 1 to 10 equivalents per 1 equivalent of the compound [I-d]. A reaction solvent used in the step (q) is not particularly limited so long as it does not badly influencing the reaction, and there can, for example, be used halogenated hydrocarbons such as dichloromethane and chloroform, ethers such as diethyl ether, tert-butyl methyl ether and tetrahydrofuran, amides such as dimethylformamide and dimethylacetamide, sulfoxides such as dimethyl sulfoxide, nitrites such as acetonitrile, alcohols such as methanol, ethanol and propanol, aromatic hydrocarbons such as benzene, toluene and xylene, water and mixed solvents thereof. There is no particular limitation about the reaction temperature and reaction time, but the reaction is carried out at a reaction temperature of the order of −10 to 100° C., preferably 0 to 50° C. for a time of the order of 1 to 20 hours, preferably 1 to 5 hours. In the step (r), the resulting aniline derivative [I-e] is subjected to a deamination reaction via a diazonium cation according to a known method or a method based thereon to give the compound [I-f].

The compounds [I-d], [I-e] and [I-f], compounds of the invention, obtained in the above steps (p), (q) and (r) can be isolated and purified, according to conventional methods, by known separation and purification means such as, for example, concentration, concentration under reduced pressure, crystallization, solvent extraction, reprecipitation, chromatography, etc.

In each of the above formulae, depending on substituent (s) which $R^5$ and Ar have, there arise cases where protection and removal of the protective group(s) get necessary. For example, when $R^5$ is an aralkyl group, as substituents requiring protection, a hydroxyl group, a carboxyl group, an amino group, a lower alkylamino group, etc., and when a hydroxyl group is used, as its protective groups, there can, for example, be used a lower alkyl group, a phenyl group, a benzyl group, a lower alkylcarbonyl group, a benzyloxycarbonyl group, a silyl group, etc. Protection and removal of the protective group on each substituent can be carried out according to methods described in the aforementioned T. W. Green and P. G. M. Wuts, Protective Groups in Organic Synthesis, 1991, etc.

It goes without saying that the reaction condition, reagents, etc. in the reaction of each step mentioned above can appropriately be changed. Further, the reaction of each step can be carried out in the presence of a solvent or in the absence of a solvent, depending on the property of the reaction and the kind of reagents. When a solvent is used, there is no particularl limitation about the solvent so long as it does not badly influencing the reaction and dissolves the starting compound in some extent, and there can, for example, be used aliphatic hydrocarbons such as hexane and heptane, aromatic hydrocarbons such as benzene, toluene and xylene, halogenated hydrocarbons such as dichloromethane, chloroform, carbon tetrachloride and dichloroethane, esters such as ethyl acetate,ethyl formate and propyl acetate, ethers such as diethyl ether, diisopropyl ether, dioxane and tetrahydrofuran, alcohols such as methanol, ethanol, n-propanol isopropanol, ketones such as acetone and methyl ethyl ketone, nitriles such as acetonitrile and propiononitrile, amides such as dimethylformamide and dimethylacetamide, sulfoxides such as dimethyl sulfoxide, etc.

Next, an orexin receptor antagonistic action which the compounds of the invention represented by the general formula [I] show, and a test method for it are set forth below.

It was demonstrated by an inhibition test of the increase in intracellular calcium concentration due to orexin shown below that the compounds of the invention represented by the general formula [I] have an excellent $OX_2$ receptor antagonistic action.

(Test Method)

A cDNA sequence encoding human orexin $OX_1$ receptor or $OX_2$ receptor (see GenBank, accession number AF 041243 and AF 041245) was cloned into the EcoRV-EcoRI site of a mamal expressed plasmid vector pIRESIneo (made by Clontech Laboratories, Inc.) and the PmlI-XbaI site of a mamal expressed plasmid vector pEF/myc/cyto (made by Invitrogen Corp.). The resulting vectors were respectively transfected into Chinese hamster's ovarian cells CHO-K1 (Americam Type Culture Collection, ATCC number CCL-61). Then, cells having resistance to 2 mg/ml of Geneticin (G418, made by Life Technologies, Inc.) were selected to obtain a cell line stably expressing a human $OX_1$ receptor and a cell line stably expressing a human $OX_2$ receptor. The $OX_1$ receptor or $OX_2$ receptor stably expressing cells were made to take up fluo-3, AM (made by Molecualr Probes Inc.), a fluorescent indicator of calcium concentration, and then 0.3 nM of orexin A was added to a suspension of the cells in an assay buffer (Hank's equilibrium salt solution adjusted to pH 7.4 and containing 20 mM HEPES, 0.5% bovine serum albumin and 2.5 mM probenecid), and the change of the intracellular calcium concentration was measured with time lapse using FLIPR (Fluorometric Imaging Plate Reader, made by Molecular Devices Corp.). The effect of a test compound influencing the increase in the intracellular calcium concentration was assayed by adding the test compound in various concentrations to the assay solutions, 5 minutes before the addition of orexin A, and the 50% inhibition concentration ($IC_{50}$ value) of the test compound against the increase in intracellular calcium concentration caused by the addition of 0.3 nM orexin A was determined (Table 1).

TABLE 1

Antagonistic action on orexin receptors

| | 50% Inhibition concentration ($\mu$M) | |
|---|---|---|
| Test compound No. | $OX_1$ receptor | $OX_2$ receptor |
| 4 | 5.3 | 0.031 |
| 6 | 24 | 0.110 |
| 8 | 17 | 0.049 |
| 23 | 4.4 | 0.140 |

(Test Compound No. Means the Compound Number in Each Example)

As shown above, the compounds of the invention strongly inhibited, at a 50% inhibition concentration of the order of $10^{-8}$ to $10^{-7}$ M, the increase in intracellular calcium concentration due to orexin A in the cells expressing an $OX_2$ receptor. On the other hand, the 50% inhibition concentrations of the compounds of the invention against the increase in intracellular calcium concentration in the $OX_1$ receptor expressing cells were 30 to more than 300 times higher than that in the $OX_2$ receptor expressing cells. Thus, it was revealed that the action of the compounds of the invention is $OX_2$ receptor-selective.

Solid pharmaceutical preparations such as tablets, capsules, granules and powders can be prepared using compounds of the invention alone, but can also be prepared using suitable additives. As such additives, there can be mentioned conventional additives, for example, sugars such as lactose and glucose, starches from corn, wheat, rice or the like, fatty acids such as stearic acid, inorganic salts such as magnesium aluminate and anhydrous calcium phosphate, synthetic macromolecules such as polyvinylpyrrolidone and polyalkylene glycols, fatty acid salts such as calcium stearate and magnesium stearate, alcohols such as stearyl alcohol and benzyl alcohol, synthetic cellulose derivatives such as methylcellulose, carboxymethylcellulose, ethylcellulose and hydroxypropylmethylcellulose, and further, water, gelatin, talc, vegetable oils, gum arabic, etc. These solid pharmaceutical preparations such as tablets, capsules, granules and powders can contain, generally 0.1 to 100% by weight, preferably 5 to 100% by weight of the active ingredient.

Liquid pharmaceutical preparations can be prepared as forms of suspensions, syrups, injections, etc. using suitable additives usually used in liquid pharmaceutical preparations, such as water, alcohols or vegetable oils including soybean oil, peanut oil and sesame oil. Particularly, as solvents suitable when the liquid pharmaceutical preparations are parenterally administered by intramuscular injection, intravenous injection or subcutaneous injection, there can, for example, be mentioned distilled water for injection, aqueous lidocaine hydrochloride solution (for intramuscular injection), physiological saline, aqueous glucose solution, ethanol, liquids for intravenous injection (e.g., aqueous solutions of citric acid, sodium citrate, etc.), electrolyte solutions (e.g., for intravenous injection by drip, for intravenous injection), etc., or their mixed solutions. These injections can be in the form of previously prepared solutions, or in the form of powder with/without suitable additives which powder is dissolved when used. These injections contain usually 0.1 to 10% by weight, preferably 1 to 5% by weight of an active ingredient. The liquid preparations such as suspensions and syrups for oral administration contain 0.5 to 10% by weight of an active ingredient.

It should be noted that the actually preferred dose of the compounds of the invention is varied depending on the symptoms, ages, the distinction of sex of patients, kinds of compounds used, compositions prepared, etc. For example, the dose of each compound per day and per one adult is 10 to 500 mg in the case of oral administration, and 10 to 100 mg in the case of parenteral administration. The frequency of administration is varied depending on administration methods and symptoms, but 1 to 5 times.

BEST MODE FOR CARRYING OUT THE INVENTION

The invention is further specifically described below according to examples, but the invention should not be limited only to these examples.

The meaning of abbreviations in nuclear magnetic resonance spectra are shown below;
s: singlet, d: doublet, dd: double doublet, t: triplet, m: multiplet, br: broad, J: coupling constant, Hz: hertz Preparation processes of starting compounds being used for preparation of compounds of the invention are shown below as reference examples.

Reference Example 1

2-(Tert-butoxycarbonylamino)-3,3-dimethylbutanoic acid

Triethylainine (3.5 ml, 25.1 mmol) and di-tert-butyl dicarbonate (2.18 g, 9.99 mmol) were added into a DMF (10 ml)

suspension of 2-amino-3,3-dimethylbutanoic acid (1.01 g, 7.72 mmol), and the mixture was stirred at room temperature for 15 hours. The mixture was concentrated under reduced pressure, the residue was dissolved in ethyl acetate (50 ml), and the solution was extracted with saturated aqueous sodium bicarbonate solution (50 ml×3). 6 N hydrochloric acid was added to the collected aqueous layer, and the mixture was, after adjustment to pH 3, extracted with chloroform (50 ml×3). The collected chloroform layer was dried over anhydrous magnesium sulfate, and filtered. The filtrate was concentrated under reduced pressure to obtain a colorless oily substance (1.95 g).

$^1$H NMR(300 MHz,CDCl$_3$) δ ppm: 1.03(s,9H), 1.42(s, 9H), 4.21(d,1H,J=10.0 Hz), 5.34(d,1H,J=10.0 Hz)

Reference Example 2

(2S)-2-(tert-butoxycarbonylamino)-3,3-dimethylbutanoicoic acid

The captioned compound was obtained from (2S)-2-amino-3,3-dimethylbutanoic acid in the same manner as in Reference example 1.

Reference Example 3

(2R)-2-(tert-butoxycarbonylamino)-3,3-dimethylbutanoic acid

The captioned compound was obtained from (2R)-2-amino-3,3-dimethylbutanoic acid in the same manner as in Reference example 1.

Reference Example 4

N-[2-(6,7-dimethoxy-1,2,3,4-tetrahydroisoquinolin-2-yl)-2-oxo-(1-tert-butyl)ethyl](tert-butoxy) carboxyamide 2-Tert-butoxycarbonylamino-3,3-dimethylbutanoic acid (1.95 g, 8.43 mmol) obtained in Reference example 1 was added to a dichloromethane (30 ml) suspension of 6,7-dimethoxy-1,2,3,4-tetrahydroisoquinoline hydrochloride (1.82 g, 7.92 mmol), and the mixture was stirred for 5 minutes. Diisopropylethylamine (4.1 ml, 23.54 mmol), bromotrispyrrolidinophosphonium hexafluorophosphate (PyBrop, 3.6 g, 7.72 mmol) and 4-(N,N-dimethylamino) pyridine (102 mg, 0.84 mmol) were added to the mixture, and the mixture was stirred at room temperature for 15 hours. The reaction solution was diluted with chloroform (50 ml), washed with water (50 ml), 1 N hydrochloric acid (50 ml) and 1 N aqueous sodium hydroxide solution (50 ml), and dried over anhydrous magnesium sulfate. The insoluble matter was filtered off and the filtrate was concentrated. The residue was purified by silica gel column chromatography using a mixed solvent of ethyl acetate and hexane (1:1) as an eluent to obtain the captioned compound (3.43 g, 100%) as a colorless oily substance.

$^1$H NMR(300 MHz,CDCl$_3$) δ ppm: 0.96 and 0.99(s each, 9H), 1.43(s,9H), 2.72–2.93(m,2H), 3.53–4.03(m,8H), 4.48–4.85(m,3H), 5.30–5.45(m,1H), 6.61 and 6.62(s each, 2H)

Reference Example 5

N-(2S)-[2-(tert-butoxycarbonylamino)-3,3-dimethylbutyryl]-6,7-dimethoxy-1,2,3,4-tetrahydroisoquinoline The captioned compound was obtained in the same manner as in Reference example 4 from (2S)-2-tert-butoxycarbonylamino-3,3-dimethylbutanoic acid obtained in Reference example 2.

Reference Example 6

N-(2R)-[2-(tert-butoxycarbonylamino)-3,3-dimethylbutyryl]-6,7-dimethoxy-1,2,3,4-tetrahydroisoquinoline The captioned compound was obtained in the same manner as in Reference example 4 from (2R)-2-tert-butoxycarbonylamino-3,3-dimethylbutanoic acid obtained in Reference example 3.

Reference Example 7

N-(2-amino-3,3-dimethylbutyryl)-6,7-dimethoxy-1,2,3,4-tetrahydroisoquinoline hydrochloride N-[2-(tert-butoxycarbonyl)amino-3,3-dimethylbutyryl]-6,7-dimethoxy-1,2,3,4-tetrahydroisoquinoline (3.43 g) obtained in Reference example 4 was dissolved in a 4 M hydrogen chloride-ethyl acetate solution (150 ml), and the solution was stirred at room temperature for 10 hours. The reaction solution was concentrated under reduced pressure, and the residue was suspended in a diethyl ether (500 ml) solution. The resulting pale yellow powder was taken by filtration, and dried at room temperature under reduced pressure to obtain the captioned compound (1.80 g, 80%).

$^1$H NMR(300 MHz,DMSO-d6) δ ppm: 0.85 and 0.91(s each,9H), 2.48–2.97(m,3H), 3.25(brs,3H), 3.52–3.89(m, 8H), 4.35–4.72(m,2H), 6.70,6.72, 6.76 and 6.80(s each,2H)

Reference Example 8

N-[(2S)-2-amino-3,3-dimethylbutyryl]-6,7-dimethoxy-1,2,3,4-tetrahydroisoquinoline hydrochloride The captioned compound was obtained in the same manner as in Reference example 7 from N-[(2S)-2-(tert-butoxycarbonylamino)-3,3-dimethylbutyryl]-6,7-dimethoxy-1,2,3,4-tetrahydroisoquinoline obtained in Reference example 5.

Reference Example 9

N-[(2R)-2-amino-3,3-dimethylbutyryl]-6,7-dimethoxy-1,2,3,4-tetrahydroisoquinoline hydrochloride The captioned compound was obtained in the same manner as in Reference example 7 from N-[(2R)-2-(tert-butoxycarbonyl)amino-3,3-dimethylbutyryl]-6,7-dimethoxy-1,2,3,4-tetrahydroisoquinoline obtained in Reference example 6.

Reference Example 10

N-[2-(6,7-dimethoxy-1,2,3,4-tetrahydroisoquinolin-2-yl)-2-oxo-1-benzylethyl](tert-butoxy) carboxyamide 6,7-Dimethoxy-1,2,3,4-tetrahydroisoquinoline hydrochloride (150 mg, 0.66 mmol) was dissolved in dichloromethane (10 ml), and 2-[(tert-butoxy)carbonylamino]-3-phenylpropionic acid (150 mg, 0.50 mmol), benzotriazol-1-yloxy-6-tripyrrolidinophosphonium hexafluorophosphate (PyBOP, 408 mg, 0.78 mmol), N-hydroxybenzotriazole (240 mg, 1.57 mmol) and diisopropylethylamine (0.41 ml, 2.35 mmol) were added, and the mixture was stirred at room temperature. One hour thereafter, the reaction mixture was washed successively with a saturated aqueous ammonium chloride solution and a saturated aqueous sodium chloride solution, dehydrated over anhydrous sodium sulfate, and concentrated. The residue was purified by silica gel column chromatography to obtain the captioned compound (207 mg, 72%) as a white solid.

$^1$H NMR(300 MHz,CDCl$_3$) δ ppm: 1.42(s,9H), 2.38(brd, 1H,J=27Hz), 2.68(m,2H), 2.96–3.00(m,2H), 3.16(m,1H), 3.83(s,3H), 3.84(s,3H), 4.38–4.70(m,2H), 4.90(m,1H), 5.47 (t,1H,J=3H), 6.30–7.25(m,7H)

Reference Example 11

N-[(2S)-2-(6,7-dimethoxy-1,2,3,4-tetrahydroisoquinolin-2-yl)-2-oxo-1-benzylethyl](tert-butoxy)carboxyamide The captioned compound was obtained in the same manner as in Reference example 10 from (2S)-2-[(tert-butoxy)carbonylamino]-3-phenylpropionic acid.

Reference Example 12

N-[(2R)-2-(1,2,3,4-tetrahydroisoquinolin-2-yl)-2-oxo-1-benzylethyl](tert-butoxy)carboxyamide The captioned compound was obtained in the same manner as in Reference example 10 from (2R)-2-[(tert-butoxy)carbonylamino]-3-phenylpropionic acid.

Reference Example 13

2-Amino-1-(6,7-dimethoxy-1,2,3,4-tetrahydroisoquinolin-2-yl)-3-phenylpropan-1-one N-[2-(6,7-dimethoxy-1,2,3,4-tetrahydroisoquinolin-2-yl)-2-oxo-1-benzylethyl](tert-butoxy)carboxyamide (207 mg, 0.47 mmol) obtained in Reference example 10 was dissolved in a dichloromethane solution (1.5 ml), trifluoroacetic acid (1 ml) was added, and the mixture was stirred at room temperature. Four hours thereafter, the reaction mixture was concentrated, diluted with a chloroform solution, and washed three times with an aqueous sodium bicarbonate solution. The organic layer was dehydrated over sodium sulfate and concentrated to obtain the captioned compound (332 mg) as a yellow oily substance.

$^1$H NMR(200 MHz,CDCl$_3$) δ ppm: 2.35–2.50(m,1H), 2.62–3.06(m,4H), 3.30–3.60(m,2H), 3.85(s,3H), 3.86(s,3H), 3.90–4.10(m,2H), 4.40–4.70(m,2H), 6.39–6.61(m,2H), 7.10–7.20(m,5H)

Reference Example 14

(2S)-2-amino-1-(1,2,3,4-tetrahydroisoquinolin-2-yl)-3-phenylpropan-1-one

The captioned compound was obtained in the same manner as in Reference example 13 from N-[(2S)-2-(6,7-dimethoxy-1,2,3,4-tetrahydroisoquinolin-2-yl)-2-oxo-1-benzylethyl](tert-butoxy)carboxyamide obtained in Reference example 11.

Reference Example 15

(2R)-2-amino-1-(6,7-dimethoxy-1,2,3,4-tetrahydroisoquinolin-2-yl)-3-phenylpropan-1-one The captioned compound was obtained in the same manner as in Reference example 13 from N-[(2R)-2-(6,7-dimethoxy-1,2,3,4-tetrahydroisoquinolin-2-yl)-2-oxo 1-benzylethyl](tert-butoxy)carboxyamide obtained from Reference example 12.

Reference Example 16

1-(6,7-Dimethoxy-1,2,3,4-tetrahydroisoquinolin-2-yl)-3-methyl-2-bromobutan-1-one Racemic body α-bromoisovaleryl chloride (327 mg, 1.64 mmol) on the market and 4-(N,N-dimethylamino)pyridine (about 10 mg) were added to a pyridine (8 ml) suspension of 6,7-dimethoxy-1,2,3,4-tetrahydroisoquinoline hydrochloride (472 mg, 2.05 mmol), and the mixture was stirred at room temperature for 3 hours. The reaction solution was diluted with chloroform (50 ml), washed with 1 N hydrochloric acid (50 ml) and a 1 N aqueous sodium hydroxide solution (50 ml), dried over anhydrous magnesium sulfate, concentrated under reduced pressure, and used, without isolating and purifying the obtained gummy substance, in the reactions in Examples 27 and 28.

Reference Example 17

2-Benzyl-6,7,8-trimethoxy-2,3,4-trihydroisoquinolin-1-one

1-Ethyl-3-(3-dimethylaminopropyl)carbodiimide hydrochloride (10.5 g, 54.68 mmol), benzylamine (6.8 g, 63.46 mmol) and a catalytic amount of 4-(N,N-dimethylamino) pyridine were added to a pyridine (150 ml) solution of (3,4,5-trimethoxyphenyl)acetic acid (9.8 g, 43.32 mmol), and the mixture was stirred at room temperature for 10 hours. The mixture was concentrated under reduced pressure, and the residue was diluted with chloroform (350 ml) and washed with water (300 ml), 1 N hydrochloric acid (300 ml) and a 1 N aqueous sodium hydroxide solution (300 ml). The organic layer was dried over anhydrous magnesium sulfate, and concentrated under reduced pressure to obtain a yellow solid. The yellow solid was dissolved in THF (350 ml), lithium aluminum hydride (4.23 g, 111.5 mmol) was added, and the mixture was stirred at room temperature for 30 minutes and refluxed with heating for 90 minutes. The reaction solution was cooled to room temperature, sodium sulfate 10 hydrate (40 g) and a small amount of a saturated aqueous potassium fluoride solution were added, and the mixture was intensely stirred at room temperature for 30 minutes. Magnesium sulfate (80 g) was added to the reaction mixture, the mixture was intensely stirred at room temperature for 15 minutes, the inorganic substance was filtered off, and the residue was sufficiently washed with ethyl acetate. The filtrate was concentrated under reduced pressure to obtain a brown oily substance. The oily substance was dissolved in chloroform, methyl chloroformate (10 ml, 129.4 mmol) and 4-(N,N-dimethylamino)pyridine (9.78 g, 80.1 mmol) were added, and the mixture was stirred at room temperature for 1 hour. The reaction solution was washed with 1 N hydrochloric acid (300 ml), the aqueous layer was extracted three times with chloroform (each 100 ml), and the collected organic layer was dried over anhydrous magnesium sulfate and concentrated under reduced pressure.

The residue was dissolved in phosphorus oxychloride (100 ml), diphosphorus pentoxide (22 g) was added, and the resulting suspension was refluxed with heating for 2 hours. The reaction solution was cooled to room temperature and phosphorus oxychloride was distilled off under reduced pressure. Ice was added by portions to the residue, and a 1 N aqueous sodium hydroxide solution was added to the mixture to neutralize it. The mixture was extracted 5 times with chloroform (each 100 ml), and the collected organic layer was dried over anhydrous magnesium sulfate and concentrated under reduced pressure. The residue was purified by silica gel column chromatography using ethyl acetate and hexane (1:3 to 3:1) as an eluent to obtain the captioned compound (8.75 g, 62%).

$^1$H NMR(300 MHz,CDCl$_3$) δ ppm: 2.79(t,2H,J=7.1 Hz), 3.38( t,2H,J=7.1 Hz), 3.88(s,6H), 4.00(s,3H), 4.79(s,2H), 6.43(s,1H), 7.25–7.38(m,5H)

Reference Example 18

6,7,8-Trimethoxy-1,2,3,4-tetrahydroisoquinoline

Lithium aluminum hydride (2.6 g, 68.9 mmol) was added to a THF (100 ml) solution of 2-benzyl-6,7,8-trimethoxy-2,3,4-trihydroisoquinolin-1-one (8.75 g, 26.7 mmol) obtained in Reference example 17, and the mixture was stirred at room temperature for 30 minutes and refluxed with heating for 90 minutes. The reaction solution was cooled to room temperature, sodium sulfate 10 hydrate (26 g) and a small amount of a saturated aqueous potassium fluoride solution were added, and the mixture was intensely stirred at room temperature for 30 minutes. Magnesium sulfate (50 g) was added to the reaction mixture, the mixture was intensely stirred at room temperature for 15 minutes, the inorganic substance was filtered off, and the residue was sufficiently washed with ethyl acetate. The filtrate was concentrated under reduced pressure to obtain a colorless oily substance. The oily substance was dissolved in ethanol (200 ml), 10% palladium-carbon catalyst (870 mg) was added, and the mixture was intensely stirred at room temperature for 10 hours under a 1 atom hydrogen atmosphere. The palladium-carbon was filtered off, and the filtrate was concentrated under reduced pressure to obtain the captioned compound (6.0 g, 100%) as a brown solid.

$^1$H NMR(300 MHz,CDCl$_3$) δ ppm: 3.09(brs,2H), 3.39 (brs,2H), 3.82(s,3H), 3.83(s,3H), 3.91(s,3H), 4.23(brs,2H), 6.41(s,1H)

EXAMPLE 1

N-[2-(N-benzoyl)amino-3,3-dimethylbutyryl]-6,7-dimethoxy-1,2,3,4-tetradroisoquinoline Benzoyl chloride (20 μl, 0.172 mmol) and a catalytic amount of 4-(N,N-dimethylamino)pyridine were added to a pyridine (3 ml) solution of N-(2-amino-3,3-dimethylbutyryl)-6,7-dimethoxy-1,2,3,4-tetrahydroisoquinoline hydrochloride (39.8 mg, 0.130 mmol) obtained in Reference example 7, and the mixture was stirred at room temperature for 2 hours. The reaction solution was diluted with chloroform, and washed with 1 N hydrochloric acid (50 ml×2). The organic layer was dried over anhydrous magnesium sulfate, the insoluble matter was filtered off, and the filtrated was concentrated. The residue was subjected to thin layer silica gel column chromatography using ethyl acetate and hexane (2:1) as an eluent to obtain the captioned compound (38.5 mg, 72.1%) as a colorless foamy substance.

$^1$H NMR(300 MHz,CDCl$_3$) δ ppm: 1.06 and 1.12 (s each,9H), 2.76–2.97(m,2H), 3.66–4.13(m,8H), 4.52–4.82 (m,2H), 5.23 and 5.27(s each,1H), 6.61–6.66(m,2H), 7.41–7.53(m,3H), 7.79–7.84(m,2H)

EXAMPLE 2

N-[2-(6,7-dimethoxy-1,2,3,4-tetrahydroisoquinolin-2-yl)-2-oxo-1-benzylethyl](3,4-dimethylphenyl) carboxyamide 2-Amino-1-(6,7-dimethoxy-1,2,3,4-tetrahydroisoquinolin-2-yl)-3-phenylpropan-1-one (32 mg, 0.09 mmol) obtained in Reference example 13 was dissolved in dichloromethane (1 ml), and then diisopropylethylamine (0.059 ml, 0.34 mmol), bromotrispyrrolidinophosphonium hexafluorophosphate (PyBrop, 57 mg, 0.12 mmol) and 3,4-dimethylberzoic acid (21 mg, 0.14 mmol) were successively added, and the mixture was stirred at room temperature. Thereafter, the same post-treatment as in Example 1 was carried out to obtain the captioned compound (18.6 mg, 43%) as a colorless solid.

$^1$H NMR(300 MHz,CDCl$_3$) δ ppm: 2.30(s,6H), 2.70(m, 1H), 3.10–3.30(m,2H), 3.55–3.80(m,1H), 3.84(s,6H), 3.99 (d,1H,J=21 Hz), 4.41–4.73(m,2H), 5.42(brs,1H), 6.35–6.60 (m,2H), 7.10–7.20(m,5H), 7.49–7.59(m,2H)

EXAMPLE 3

N-[(2R)-2-(6,7-dimethoxy-1,2,3,4-tetrahydroisoquinolin-2-yl)-2-oxo-1-benzylethyl]-benzamide (2R)-2-amino-1-(6,7-dimethoxy-1,2,3,4-tetrahydroisoquinolin-2-yl)-3phenylpropan-1-one (79 mg, 0.23 mmol) obtained in Reference example 15 was dissolved in a dichloromethane solution (2 ml), and then triethlamine (0.096 ml, 0.69 mmol) and benzoyl chloride (0.04 ml, 0.35 mmol) were successively added, and the mixture was stirred at room temperature. Thereafter, the same post-treatment as in Example 1 was carried out to obtain the captioned compound (52 mg, 51%).

$^1$H NMR(200 MHz,CDCl$_3$) δ ppm: 2.35(brs,1H), 3.15(m, 2H), 3.65(m,2H), 3.84(s,3H), 3.85(s,3H), 4.00(d,1H,J=24 Hz), 4.60(m,3H), 5.54(brs,1H), 6.50(m,2H), 7.20(m,4H), 7.45(m,5H), 7.80(d,3H,J=6 Hz)

The compound of Example 4 was obtained in the same manner as in Example 3.

EXAMPLE 4

N-[2-(6,7-dimethoxy-1,2,3,4-tetrahydroisoquinolin-2-yl)-2-oxo-1-benzylethyl](3,5-dichlorophenyl) carboxyamide $^1$H NMR(200 MHz,CDCl$_3$) δ ppm: 2.71(brs,1H), 3.19(m, 1H), 3.85(s,3H), 3.86(s,3H), 4.10(m,1H), 4.65(m,2H), 5.48 (m,1H), 6.55(m,2H), 7.20(m,4H), 7.49(s,1H), 7.65(s,2H)

EXAMPLE 5

N-(6,7-dimethoxy-1,2,3,4-tetrahydroisoquinolin-2-yl)-(2S)-(benzylamino)-3-phenylpropan-1-one (2S)-2-amino-1-(6,7-dimethoxy-1,2,3,4-tetrahydroisoquinolin-2-yl)-3phenylpropan-1-one (21 mg, 0.06 mmol) obtained in Reference example 14 was dissolved in a dichloroethane (1 ml), and then benzaldehyde (0.01 ml, 0.12 mmol) and sodium triacetoxyborohydride (37 mg, 0.18 mmol) were successively added, and the mixture was stirred at room temperature. Three hours thereafter, the mixture was washed with a saturated aqueous ammonium chloride solution, dehydrated with anhydrous sodium sulfate, and concentrated. The residue was purified by silica gel column chromatography to obtain the captioned compound (17 mg, 63%) as a colorless oily substance.

$^1$H NMR(300 MHz,CDCl$_3$) δ ppm: 2.09(m,4H), 2.46(m, 1H), 2.68(m,1H), 2.93(m,4H), 3.27(m,1H), 3.55(dd,1H,J= 3,24 Hz), 3.80(m,6H), 4.11(d,1H,J=24 Hz), 4.45(d,1H,J=24 Hz), 4.75(d,1H,J=24 Hz), 6.50(m,2H), 7.20(m,10H)

EXAMPLE 6

(2S)-2-(N-4-pyridylmethyl)amino-1-(6,7-dimethoxy-1,2,3,4-tetrahydroisoquinolin-2yl)-3,3-dimethylbutan-1-one 4-Pyridinecarboxyaldehyde (20 μl, 0.21 mmol) and sodium triacetoxyborohydride (50 mg, 0.24 mmol) were added to a dichloromethane (2 ml) solution of N-[(2S)-amino-3,3-dimethylbutyryl]-6,7-dimethoxy-1,2,3,4-tetrahydroisoquinoline hydrochloride (30 mg, 0.10 mmol) obtained in Reference example 8, and the mixture was stirred at room temperature for 10 hours. A 1 N aqueous sodium hydroxide solution (1 ml) was added to the reaction mixture, the mixture was stirred for 30 minutes, and the reaction was discontinued. The organic layer was separated and concentrated under reduced pressure. The residue was purified by silica gel column chromatography using chloroform and methanol (30:1) as an eluent to obtain the captioned compound (19.8 mg, 48%) as colorless crystals.

$^1$H NMR(300 MHz,CDCl$_3$) δ ppm: 0.97 and 1.02(s each, 9H), 2.61–2.90(m,2H), 3.20–3.51(m,3H), 3.62–4.13(m,8H), 4.31–4.99(m,2H), 6.40, 6.66,6.64 and 6.65(s each,2H), 7.09–7.32(m,2H), 8.40–8.56(m,2H)

EXAMPLE 7

(2R)-2-(N-4-pyridylmethyl)amino-1-(6,7-dimethoxy-1,2,3,4-tetrahydroisoquinolin-2-yl)-3,3-dimethylbutan-1-one The captioned compound was obtained in the same manner as in Example 6 using N-[(2N)-amino-3,3-dimethylbutyryl] -6,7-dimethoxy-1,2,3,4-tetrahydroisoquinoline hydrochloride obtained in Reference example 9.

The compounds of Examples 8 to 21 were obtained in the same manner as in Example 6.

EXAMPLE 8

(2S)-1-(6,7-dimethoxy-1,2,3,4-tetrahydroisoquinolin-2-yl)-3,3-dimethyl-2-((2-thiazolylmethyl)amino)butan-1-one $^1$H NMR(300 MHz,CDCl$_3$) δ ppm: 0.99 and 1.03(s each, 9H), 2.68–2.92(m,2H), 3.32–4.02(m,10H), 4.08–4.17(m, 1H), 4.46–4.97(m,2H), 6.51,6.61 and 6.63(s each,2H), 7.23 and 7.26(d each,1H,J=3.3 Hz), 7.58 and 7.66(d each,1H,J= 3.3 Hz)

EXAMPLE 9

(2S)-1-(6,7-dimethoxy-1,2,3,4-tetrahydroisoquinolin-2-yl)-3,3-dimethyl-2-((3-phenylpropyl)amino)butan-1-one $^1$H NMR(300 MHz,CDCl$_3$) δ ppm: 0.97 and 0.99(s each, 9H), 1.60–2.11(m,2H), 2.25–2.40(m,1H), 2.48–3.05(m,6H), 3.24–3.39(m,1 H), 3.52–4.01(m,7H), 4.42–5.02(m,2H), 6.56,6.61 and 6.63(s each,2H), 7.02–7.33(m,5H)

EXAMPLE 10

(2S)-2-(2-chloro-5-nitrobenzyl)amino-1-(6,7-dimethoxy-1,2,3,4-tetrahydroisoguinolin-2-yl)-3,3-dimethylbutan-1-one $^1$H NMR(300 MHz,CDCl$_3$) δ ppm: 1.01 and 1.05(s each, 9H), 2.65–2.81(m,2H), 3.48–4.01(m,11H), 4.39–4.95(m, 2H), 6.40,6.59,6.60 and 6.62(s each,2H), 7.36 and 7.47(d each, 1H,J=8.5 Hz), 7.95 and 8.01(dd each,1H,J=2.6 and 8.5 Hz), 8.43and 8.52(d each,1H, J=2.6 Hz)

EXAMPLE 11

(2S)-2-(2-guinolylmethyl)amino-1-(6,7-dimethoxy-1,2,3,4-tetrahydroisoquinolin-2-yl)-3,3-dimethylbutan-1-one $^1$H NMR(300 MHz,CDCl$_3$) δ ppm: 0.96 and 0.99(s each, 9H), 2.59–2.88(m,2H), 3.29–3.51(m,2H), 3.67–4.18(m,9H), 4.33–4.89(m,2H), 6.31,6.54,6.56 and 6.60(s each,2H), 7.43–8.11(m,6H)

EXAMPLE 12

(2S)-2-(2-(5-bromo-2-thienyl)methyl)amino-1-(6,7-dimethoxy-1,2,3,4-tetrahydroisoquinolin-2-yl)-3,3-dimethylbutan-1-one $^1$H NMR(300 MHz,CDCl$_3$) Δ ppm: 0.98 and 1.01(s each,9H), 2.68–2.91(m,2H), 3.38–4.19(m,11H), 4.41–5.00 (m,2H), 6.22–6.87(m,4H)

EXAMPLE 13

(2S)-2-(2-(5-ethyl-2-furyl)methyl)amino-1-(6,7-dimethoxy-1,2,3,4-tetrahydroisoquinolin-2-yl)-3,3-dimethylbutan-1-one $^1$H NMR(300 MHz,CDCl$_3$) δ ppm: 0.94 and 0.98(s each, 9H), 1.13–1.25(m,3H), 2.51–2.68(m,2H), 2.70–2.82(m,2H), 3.20–4.01 (m, 11H), 4.48–4.92(m,2H), 5.73–6.06(m,2H), 6.53,6.61 and 6.63(s each,2H)

EXAMPLE 14

(2S)-2-(2-(5-nitro-2-furyl)methylamino)-1-(6,7-dimethoxy-1,2,3,4-tetrahydroisoquinolin-2-yl)-3,3-dimethylbutan-1-one $^1$H NMR(300 MHz,CDCl$_3$) δ ppm: 0.96 and 1.01(s each, 9H), 2.72–2.84(m,2H), 3.38–3.66(m,3H), 3.75–3.94(m,8H), 4.43–4.98(m,2H), 6.37 and 6.48(d each,1H,J=3.6 Hz), 6.56, 6.61 and 6.62(s each,2H), 7.16 and 7.21(d each,1H,J=3.6 Hz)

EXAMPLE 15

3-({[2-(6,7-dimethoxy-1,2,3,4-tetrahydroisoquinolin-2-yl)-(1S)-1-(tert-butyl)-2-oxoethyl]amino}methyl)benzonitrile $^1$H NMR(300 MHz,CDCl$_3$) δ ppm: 0.97 and 1.01(s each, 9H), 2.51–2.90(m,2H), 3.20–3.55(m,3H), 3.64–4.10(m,3H), 3.85(s,3H), 3.88(s,3H), 4.33–5.01(m,2H), 6.42–6.65(m,2H), 7.18–7.76(m,4H)

EXAMPLE 16

(2S)-2-((2,4-dimethoxybenzyl)amino)-1-(6,7-dimethoxy-1,2,3,4-tetrahydroisoquinolin-2-yl)-3,3-dimethylbutan-1-one $^1$H NMR(300 MHz,CDCl$_3$) δ ppm: 0.95 and 0.99(s each, 9H), 2.57–2.77(m,2H), 3.26(d,1H,J=8.4 Hz), 3.49–3.92(m, 16H), 4.30–4.69(m,2H), 6.19–6.62(m,4H), 7.09 and 7.22(d each,1H,J=8.9 Hz)

EXAMPLE 17

2-(1-Methylbenzimidazol-2-ylmethyl)amino-1-(6.7-dimethoxy( 1,2,3,4-tetrahydroisoquinolin-2-yl))-3,3-dimethylbutan-1-one $^1$H NMR(300 MHz,CDCl$_3$) δ ppm: 0.87 and 0.91(s each, 9H), 2.27–3.01(m,2H), 3.07–3.62(m,2H), 3.67–4.15(m, 12H), 4.32–4.59(m,2H), 6.51,6.52,6.53 and 6.60(s each, 2H), 7.11–7.35(m,3H), 7.46–7.67(m,1H)

EXAMPLE 18

(2S)-2-(2H-benzo[d]1,3-dioxolen-5-ylmethyl)amino-1-(6,7-dimethoxy( 1,2,3,4-tetrahydroisoguinolin-2-yl))-3,3-dimethylbutan-1-one $^1$H NMR(300 MHz,CDCl$_3$) δ ppm: 0.96 and 1.00(s each, 9H), 2.67–2.89(m,2H), 3.22–3.78(m,3H), 3.79–4.16(m,8H), 4.39–4.95(m,2H), 5.89–5.95(m,2H), 6.43–6.91(m,5H)

EXAMPLE 19

1-(6,7-Dimethoxy(1,2,3,4-tetrahydroisoquinolin-2-yl))-(2S)-2-[(indol-3-ylmethyl)amino]-3,3-dimethylbutan-1-one $^1$H NMR(300 MHz,CDCl$_3$) δ ppm: 0.95 and 1.02(s each, 9H), 2.56–2.85(m,2H), 3.36–4.18(m,12H), 4.23–5.36(m, 2H), 6.32–6.84(m,2H), 7.00–7.39(m,3H), 7.64–8.05(m,2H)

EXAMPLE 20

2-[(2,4-Dimethoxypyrimidin-5-yl)methyl]amino-1-(6.7-dimethoxy(1,2,3,4-tetrahydroisoquinolin-2-yl))-3,3-dimethylbutan-1-one $^1$H NMR(300 MHz,CDCl$_3$) δ ppm: 0.94 and 0.99(s each, 9H), 2.68–2.80(m,2H), 3.23–3.79(m,5H), 3.80–4.02(m, 12H), 4.41–4.77(m,2H), 6.51, 6.60 and 6.62(s each,2H), 8.13 and 8.19(s each,1H)

EXAMPLE 21

1-(6,7-Dimethoxy(1,2,3,4-tetrahydroisoquinolin-2-yl))-(2S)-2-[(4-(dimethylamino)naphthalen-1-ylmethyl)amino]-3,3-dimethylbutan-1-one $^1$H NMR(300 MHz,CDCl$_3$) δ ppm: 0.91 and 0.98(s each, 9H), 2.82 and 2.85(s each,6H), 2.60–2.95(m,2H), 3.30–6.52 (m,12H), 4.38–4.96(m,2H), 6.42–6.65(m,2H), 6.72–7.35(m, 2H), 7.40–7.56(m,2H), 8.13–8.34(m,2H)

EXAMPLE 22

2-(Benzylamino)-1-(6,7-dimethoxy-1,2,3,4-tetrahydroisoquinolin-2-yl)-3,3-dimethylbutan-1-one Anhydrous potassium carbonate (120 mg), benzyl chloride (20 μl, 0.174 mmol) and a catalytic amount of potassium iodide were added to a DMF (1 ml) solution of N(2-amino-3,3-dimethylbutyryl)-6,7-dimethoxy-1,2,3,4-tetrahydroisoquinoline hydrochloride (43.2 mg, 0.141 mmol) obtained in Reference example 7, and the mixture was stirred at room temperature for 2 hours. The reaction solution was diluted with a 1:1 mixture (50 ml) of ethyl acetate and hexane, and washed with water. The organic layer was dried over anhydrous magnesium sulfate, the insoluble matter was filtered off, and the filtrate was concentrated under reduced pressure. The residue was subjected to silica gel column chromatography using ethyl acetate and hexane (2:1) as an eluent to obtain the captioned compound (33.5 mg, 59.6%) as a colorless foamy substance.

The compounds of Example 23 was obtained in the same manner as in Example 22.

EXAMPLE 23

(2S)-2-(3-bromobenzylamino)-1-(6,7-dimethoxy-1,2,3,4-tetrahydroisoquinolin-2-yl)-3,3-dimethylbutan-1-one $^1$H NMR(300 MHz,CDCl$_3$) δ ppm: 0.98 and 1.02(s each, 9H), 2.68–2.85(m,2H), 3.26–3.51(m,3H), 3.59–4.08(m,8H), 4.30–4.96(m,2H), 6.43, 6.61 and 6.64(s each,2H), 7.01–7.50 (m,4H)

EXAMPLE 24

(2S)-1-(6,7-dimethoxy-1,2,3,4-tetrahydroisoquinolin-2-yl)-3,3-dimethyl-2-((2-nitrophenyl)amino)butan-1-one Anhydrous potassium carbonate (640 mg, 4.63 mmol) and 2-fluoronitrobenzene (820 mg, 5.81 mmol) were added to a dimethyl sulfoxide (100 ml) solution of N-(2-amino-3,3-dimethylbutyryl)-6,7-dimethoxy-1,2,3,4-tetrahydroisoquinoline hydrochloride (1.05 g, 3.42 mmol) obtained in Reference example 7, and the mixture was heated at 80° C. for 90 minutes. The reaction mixture was cooled to room temperature, diluted with a diethyl ether solution (200 ml), washed with water and dried over anhydrous magnesium sulfate, and the solvent was distilled off under reduced pressure. The residue was purified by silica gel column chromatography using ethyl acetate and hexane (1:4 to 2:1) as an eluent to obtain the captioned compound (395 mg, 27%) as an orange foamy substance.

$^1$H NMR(300 MHz,CDCl$_3$) δ ppm: 1.14 and 1.16(s each, 9H), 2.76 and 2.87(t each,2H,J=5.3 Hz), 3.76–3.98(m,8H), 4.46–4.81(m,3H), 6.51–6.79(m,3H), 7.14–7.40 (m,1H), 8.11–8.21(m,1H), 8.67–8.80(m,1H)

EXAMPLE 25

(2S)-2-((2-aminophenyl)amino)-1-(6,7-dimethoxy-1,2,3,4-tetrahydroisoquinolin-2-yl)-3,3-dimethylbutan-1-one Ethanol (5 ml) and a saturated aqueous ammonium chloride solution (5 ml) were added to a tetrahydrofuran (5 ml) solution of (2S)-1-(6,7-dimethoxy-1,2,3,4-tetrahydroisoquinolin-2-yl)-3,3-dimethyl-2-((2-nitrophenyl)amino)butan-1-one (395 mg, 0.92 mmol) obtained in Example 24, and the mixture was stirred at room temperature. Water was added to the reaction solution until the insoluble matter was dissolved, powdery iron (6 g) was added, and the mixture was refluxed with heating for 2 hours. The reaction solution was cooled to room temperature, and the excessive iron and tinorganic salt were filtered off using Celite. The filtrate was diluted with ethyl acetate (150 ml), washed with a 1 N aqueous sodium hydroxide solution (50 ml×2), dried over anhydrous magnesium sulfate, and filtered. The filtrate was concentrated under reduced pressure, and the residue was purified by silica gel column chromatography using ethyl acetate and hexane (1:1) and then chloroform and methanol (20:1) as eluents to obtain the captioned compound (321 mg, 87%) as a colorless foamy substance.

$^1$H NMR(300 MHz,CDCl$_3$) δ ppm: 1.01 and 1.14(s each, 9H), 2.34–2.72(m,2H), 3.84–4.12(m,9H), 4.42–4.80(m,2H), 6.48–6.73(m,5H)

EXAMPLE 26

(2S)-2-(phenylamino)-1-(6,7-dimethoxy-1,2,3,4-tetrahydroisoquinolin-2-yl)-3,3-dimethylbutan-1-one Tetrafluoroboric acid (1.5 ml) and an aqueous sodium nitrite solution (20 mg/0.2 ml, 0.29 mmol) were added, at 0° C., to a dioxane (2 ml) solution of (2S)-2-[(2aminophenyl)amino]-1-(6,7-dimethoxy-1,2,3,4-tetrahydroisoquinolin-2-yl)-3,3dimethylbutan-1-one (100 mg, 0.25 mmol) obtained in Example 25, and the mixture was stirred at that temperature for 30 minutes. Copper (I) oxide (75 mg, 0.52 mmol) was added to the reaction solution, and the mixture was stirred for 30 minutes. Dioxane (2 ml) and water (10 ml) were added to the mixture, and the mixture was concentrated under reduced pressure. The residue was extracted twice with chloroform (each 5 ml), and the extract was dried over anhydrous magnesium sulfate and concentrated under reduced pressure. The residue was purified by silica gel thin layer chromatography using hexane and ethyl acetate (2:1) as an eluent to obtain the captioned compound (68.0 mg, 70%) as a green oily substance.

¹H NMR(300 MHz,CDCl₃) δ ppm: 1.20 and 1.26 (s each,9H), 2.53–2.69(m,2H), 3.35–4.06(m,9H), 4.44–4.82 (m,2H), 5.80(d,1H,J=7.0 Hz), 6.24,6.36,6.44 and 6.55(s each,2H), 7.19–7.42(m,2H), 7.77–8.03(m,2H)

EXAMPLE 27

1-(6.7-Dimethoxy-1,2,3,4-tetrahydroisoquinolin-2-yl)-3-methyl-2-(phenoxy)butan-1-one Phenol (50 μl, 0.569 mmol) and sodium hydride (60% in a mineral oil, 10 mg) were added to a DMF (2 ml) solution of 1-(6,7-dimethoxy-1,2,3,4-tetrahydroisoquinolin-2-yl)-3-methyl-2-bromobutan-1-one (54 mg, 0.152 mmol) obtained in Reference example 16, and the mixture was stirred at 80° C. for 10 hours and cooled to room temperature. The reaction solution was diluted with ethyl acetate and hexane (1:1, 50 ml), washed with a 1 N aqueous sodium hydroxide solution (30 ml) and 1 N hydrochloric acid (30 ml), dried over anhydrous magnesium sulfate, and concentrated under reduced pressure. The residue was subjected to preparative thin layer chromatography using ethyl acetate and hexane (1:1) as an eluent to obtain the captioned compound (30.7 mg, 55%) as a yellow oily substance.

¹H NMR(300 MHz,CDCl₃) δ ppm: 0.97–1.20 (m,6H), 2.15–2.38(m,1H), 2.53–2.88(m,2H), 3.41–3.92(m,7H), 3.98–4.17(m,1H), 4.45–5.01(m,3H), 6.49–6.61(m,2H), 6.86–7.01(m,3H), 7.18–7.29(m,2H)

The compound of Example 28 was obtained in the same manner as in Example 27.

EXAMPLE 28

1-(6,7-Dimethoxy-1,2,3,4-tetrahydroisoquinolin-2-yl)-3-methyl-2-(phenylthio)butan-1-one ¹H NMR(300 MHz,DMSO-d6 ) δ ppm: 0.79–1.09(m,6H), 1.89–2.08(m,1H), 2.48–2.65(m,2H), 3.17–3.34(m,1H), 3.42–3.78(m,8H), 4.03–4.62(m,2H), 6.58,6.63 and 6.70(s each,2H), 7.12–7.40(m,5H)

Pharmaceutical preparation examples of a compound of the invention are shown below, but pharmaceutical preparations of compounds of the invention are not limited thereto.

Pharmaceutical Preparation Example 1

Ten parts of the compound of Example 4, 15 parts of heavy magnesium oxide and 75 parts of lactose are uniformly mixed to prepare a powdery or fine granular powder having a particle size of 500 μm or less. This powder is capsulized to obtain capsules.

Pharmaceutical Preparation Example 2

Forty five parts of the compound of Example 4, 15 parts of starch, 16 parts of lactose, 21 parts of crystalline cellulose, 3 parts of polyvinyl alcohol and 30 parts of distilled water are uniformly mixed, fractured, granulated, dried, and then sieved to obtain granules having a diameter of 355 to 1,400 μm.

Pharmaceutical Preparation Example 3

Granules are prepared in the same manner as in Pharmaceutical preparation example 2. Three parts of calcium stearate are added to 96 parts of the granules, and the mixture is compression molded to obtain tablets having a diameter of 10 mm.

Pharmaceutical Preparation Example 4

Ten parts of crystalline cellulose and 3 parts of calcium stearate are added to 90 parts of granules obtained in the same manner as in Pharmaceutical preparation example 2, and the mixture is compression molded to obtain tablets having a diameter of 8 mm. Then, a suspension obtained by mixing syrup gelatin and precipitated calcium carbonate is added to the tablets to obtain sugar-coated tablets.

Industrial Applicability

Compounds represented by the general formula [I] and their pharmaceutically acceptable salts have an antagonistic action on orexin receptors, particularly on an OX₂ receptor, one of the two subtypes of orexin receptors, and, therefore, are useful as active ingredients of drugs for treatment or prophylaxis of various diseases such as, for example, appetite abnormality such as bulimia or cibophobia; obesity; diabetes; dysgeusia; sleeping disorder such as insomnia or narcolepsy; anxiety neurosis; schizophrenia; manic-depressive psychosis; insanity; dementia; serious mental retardation; dyskinesia; ache; asthma; parkinsonism; acute heart failure; hypotension; hypertension; angina pectoris; cardiac infarction; and impotence.

What is claimed is:

1. A compound represented by the formula [I]:

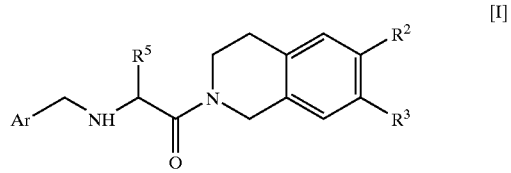

(wherein, R² and R³, each independently, represent lower alkoxy groups; R⁵ represents a benzyl group or a tert-butyl group; and Ar represents a monocyclic or bicyclic aryl or heteroaryl group optionally having substituent(s) selected from the group consisting of lower alkyl group(s), lower alkoxy group(s), halogen atom(s), halogenated lower alkyl group(s), hydroxyl group(s), carboxyl group(s), lower alkoxy carbonyl group(s), nitro group(s), amino group(s), lower alkylamino group(s), cyano group(s) and methylenedioxy group(s)), or a pharmaceutically acceptable salt thereof.

2. The compound or pharmaceutically acceptable salt thereof according to claim 1 wherein Ar is a phenyl group, a naphthyl group, a furyl group, a thienyl group, a thiazolyl group, an isothiazolyl group, an oxazolyl group, an isoxazolyl group, a pyridinyl group, a pyrazolyl group, a pyrrolyl group, a pyrimidinyl group, a quinolyl group, a quinoxalinyl group, an isoquinolyl group, a pyrazinyl group, an indolyl group, a benzothiazolyl group or a benzimidazolyl group, each of these groups optionally having substituent(s) selected from the group consisting of lower alkyl group(s), lower alkoxy group(s), halogen atom(s), halogenated lower alkyl group(s), hydroxyl group(s), carboxyl group(s), lower alkoxycarbonyl group(s), nitro group(s), amino group(s), lower alkylamino group(s), cyano group(s) and methylenedioxy group(s).

3. The compound or pharmaceutically acceptable salt thereof according to claim 2 wherein Ar is a phenyl group, a furyl group, a thienyl group, a thiazolyl group, an isothiazolyl group, an oxazolyl group, an isoxazolyl group, a pyridinyl group, a pyrazolyl group, a pyrrolyl group, a quinolyl group, a quinazolinyl group, an isoquinolyl group or a pyrazinyl group, each of these groups optionally having substituent(s) selected from the group consisting of lower alkyl group(s), lower alkoxy group(s), halogen atom(s), halogenated lower alkyl group(s), hydroxyl group(s), carboxyl group(s), lower alkoxycarbonyl group(s), nitro group (s), amino group(s), lower alkylamino group(s), cyano group (s) and methylenedioxy group(s).

4. The compound according to claim 2 wherein Ar is a phenyl group, a furyl group, a thienyl group, a thiazolyl group, pyridinyl group, a quinolyl group or a pyrrolyl group, each of these groups optionally having substituent(s) selected from the group consisting of lower alkyl group(s), lower alkoxy group(s), halogen atom(s), halogenated lower alkyl group(s), hydroxyl group(s), carboxyl group(s), lower alkoxycarbonyl group(s), intro group(s), amino group(s), lower alkylamino group(s), cyano group(s) and methylenedioxy group(s).

5. The compound or pharmaceutically acceptable salt thereof according to claim 2 wherein $R^2$ and $R^3$ are methoxy groups.

6. A pharmaceutical composition containing a therapeutically effective amount of at least one of the compounds and pharmaceutically acceptable salts thereof according to one of claims 1 to 5 as an active ingredient, and a pharmaceutically acceptable carrier.

* * * * *